US006432975B1

(12) United States Patent
Schmitt et al.

(10) Patent No.: US 6,432,975 B1
(45) Date of Patent: Aug. 13, 2002

(54) PHARMACEUTICAL COMPOSITIONS AND METHODS FOR USE

(75) Inventors: Jeffrey Daniel Schmitt, Winston-Salem, NC (US); Peter Anthony Crooks, Lexington, KY (US); Gary Maurice Dull, Lewisville, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/210,113

(22) Filed: Dec. 11, 1998

(51) Int. Cl.[7] .................. A61K 31/44; C07D 415/00; C07D 413/00; C07D 253/08

(52) U.S. Cl. .............. 514/299; 514/305; 544/133; 544/137; 544/183; 546/112

(58) Field of Search .................... 546/133, 137, 546/183, 112; 514/305, 299

(56) References Cited

U.S. PATENT DOCUMENTS

| | | | |
|---|---|---|---|
| 4,203,990 A | * 5/1980 | Yen et al. | 424/267 |
| 4,970,315 A | * 11/1990 | Schmidhalter et al. | 546/10 |
| 5,212,188 A | 5/1993 | Caldwell et al. | 514/343 |
| 5,217,975 A | 6/1993 | Wadsworth et al. | 514/299 |
| 5,219,849 A | 6/1993 | Lotti et al. | 514/214 |
| 5,276,043 A | 1/1994 | Lippiello et al. | 514/343 |
| 5,346,906 A | 9/1994 | Baker et al. | 514/305 |
| 5,510,355 A | 4/1996 | Bencherif et al. | 514/305 |
| 5,583,140 A | 12/1996 | Bencherif et al. | 514/299 |
| 5,597,919 A | 1/1997 | Dull et al. | 544/242 |
| 5,604,231 A | 2/1997 | Smith et al. | 514/256 |
| 5,616,707 A | 4/1997 | Crooks et al. | 544/242 |
| 5,616,716 A | 4/1997 | Dull et al. | 546/300 |
| 5,663,356 A | 9/1997 | Ruecroft et al. | 546/300 |
| 5,811,442 A | 9/1998 | Bencherif et al. | 514/384 |
| 5,824,692 A | 10/1998 | Lippiello et al. | 514/343 |
| 5,852,041 A | 12/1998 | Cosford et al. | 514/351 |
| 5,859,004 A | 1/1999 | Olesen | 514/214 |
| 5,861,423 A | 1/1999 | Caldwell et al. | 514/351 |
| 5,952,339 A | 9/1999 | Bencherif et al. | 514/294 |

FOREIGN PATENT DOCUMENTS

| | | |
|---|---|---|
| IN | 173570 | * 4/1996 |
| WO | WO 94/08992 | 4/1994 |
| WO | 95/03306 | 2/1995 |
| WO | WO 96/12711 | 5/1996 |
| WO | WO 97/01556 | 1/1997 |
| WO | WO 97/11072 | 3/1997 |
| WO | WO 98/25619 | 6/1998 |
| WO | WO 98/54181 | 12/1998 |
| WO | WO 99/00385 | 1/1999 |
| WO | WO 99/51602 | 10/1999 |

OTHER PUBLICATIONS

CAS Printout for In 173570, Apr. 1996.*
CAS Printout for Schmidhalter et al., Nov. 1990.*
CAS Printout for Begue et al., Dec. 1969.*
Van Dijk, Jeanette P.M. et al., "Nicotine inhibits cytokine synthesis by mouse colonic mucosa," European Journal of Pharmacology, 278, R11–R12 (1995).
Hanisch, Uwe–Karsten et al., "Modulation of Hippocampal Acetylcholine Release: A Potent Central Action of Interleukin–2," The Journal of Neuroscience, vol. 13 (8), pp. 3368–3374 (1993).
Madretsma, Stanley et al., "In–vivo effect of nicotine on cytokine production by human non–adherent mononuclear cells," European Journal of Gastroenterology & Hepatology, vol. 8, No. 10, pp. 1017–1020 (1996).
Madretsma, G.S., et al., "Nicotine inhibits the in vitro production of interleukin 2 and tumour necrosis factor–α by human monocuclear cells," Immunopharmacology, 35, pp. 47–51 (1996).
Peacock, Mark E. et al., "The Effect of Nicotine on Reproduction and Attachment of Human Gingival Fibroblasts in vitro," J. Periodontal, vol. 64, No. 7, pp. 658–665 (1993).
Sandborn, W. J. et al., "Nicotine tartrate liquid enemas for mildly to moderately active left–sided ulcerative colitis unresponsive to first–line therapy: a pilot study," Ailment Pharmacol. Ther., 11, pp. 663–671 (1997).
Zijlstra, F. J. et al., "Effect of nicotine on rectal mucus and mucosal eicosanoids," Gut, 35, pp. 247–251 (1994).
Pullan, Rupert D., "Colonic mucus, smoking and ulcerative colitis," Ann R. Coll. Surg Engl., 78, pp. 85–91 (1996).
Pullan, Robert D. et al., "Transdermal Nicotine for Active Ulcerative Colitis," The New England Journal of Medicine, vol. 330, No. 12, pp. 811–815 (1994).
Silverstein, Marc D., M.D. et al., "Cigarette Smoking and Ulcerative Colitis: A Case–Control Study", Mayo Clin. Proc., vol. 69. pp. 425–429 (1994).
Birtwistle, Jon, Postgrad Med. J., "The role of cigarettes and nicotine in the onset and treatment of ulcerative colitis," vol. 72, pp. 714–718 (1996).
Ebadi, M. et al., "Neurotrophins And Their Receptors in Nerve Injury and Repair," Neurochem Int., vol. 30, Nos. 4/5, pp. 347–374 (1997).
Matthys, Patrick Ph.D. et al., "Cytokines and Cachexia," Nutrition, vol. 13, No. 9, pp. 763–770 (1997).

(List continued on next page.)

Primary Examiner—Richard L. Raymond
Assistant Examiner—Hong Liu
(74) Attorney, Agent, or Firm—Womble Carlyle Sandridge & Rice, PLLC

(57) ABSTRACT

Pharmaceutical compositions include aryl substituted amine compounds, and in particular, carbon-linked aromatic azabicyclo compounds, and in particular, aromatic alkylene azabicyclo compounds and aromatic alkyl azabicyclo compounds.

30 Claims, No Drawings

OTHER PUBLICATIONS

Jonakait, G. Miller, TINS, "Neural–immune interactions in sympathetic ganglia," vol. 16, No. 10, pp. 419–423 (1993).

Wallace, John L. et al., "Inflammatory Mediators in Gastrointestinal Defense and Injury," Proc. Soc. Exp. Biol. Med., vol. 214, pp. 192–203 (1997).

Barnes, Peter J., Int. "Nuclear Factor-χ-B," J. Biochem. Cell Biol., vol. 29, No. 6, pp. 867–870 (1997).

Sartor, R. Balfour M.D., "Pathogenesis and Immune Mechanisms of Chronic Inflammatory Bowel Diseases," The American Journal of Gastroenterology, vol. 92, No. 12, pp. 5S–11S (1997).

International Search Report, PCT/US99/19906, Jan. 13, 2000.

Holladay, M. W. et al., *J. Med. Chem.*, vol. 40, No. 26, pp. 4169–4194 (1997).

Olesen, P. H. et al., Bioorganic & Medicinal Chemistry Letters, vol. 7, No. 15, pp. 1963–1968 (1997).

Yanina et al, Khim.–Karm, vol. 21(7), pp. 808–811 (1987).

* cited by examiner

PHARMACEUTICAL COMPOSITIONS AND METHODS FOR USE

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of acting to inhibit function of certain nicotinic cholinergic receptors, and hence acting as antagonists at certain specific nicotinic receptor subtypes. The present invention also relates to methods for treating a wide variety of conditions and disorders, including conditions and disorders associated with dysfunction of the central and autonomic nervous systems.

Nicotine has been proposed to have a number of pharmacological effects. See, for example, Pullan et al. N. Engl. J. Med. 330:811–815 (1994). Certain of those effects may be related to effects upon neurotransmitter release. See for example, Sjak-shie et al., Brain Res. 624:295 (1993), where neuroprotective effects of nicotine are proposed. Release of acetylcholine and dopamine by neurons upon administration of nicotine has been reported by Rowell et al., J. Neurochem. 43:1593 (1984); Rapier et al., J. Neurochem. 50:1123 (1988); Sandor et al., Brain Res. 567:313 (1991) and Vizi, Br. J. Pharmacol. 47:765 (1973). Release of norepinephrine by neurons upon administration of nicotine has been reported by Hall et al., Biochem. Pharmacol. 21:1829 (1972). Release of serotonin by neurons upon administration of nicotine has been reported by Hery et al., Arch. Int. Pharmacodyn. Ther. 296:91 (1977). Release of glutamate by neurons upon administration of nicotine has been reported by Toth et al., Neurochem Res. 17:265 (1992). In addition, nicotine reportedly potentiates the pharmacological behavior of certain pharmaceutical compositions used for the treatment of certain disorders. See, Sanberg et a., Pharmacol. Biochem. & Behavior 46:303 (1993); Harsing et al., J. Neurochem. 59:48 (1993) and Hughes, Proceedings from Intl. Symp. Nic. S40 (1994). Furthermore, various other beneficial pharmacological effects of nicotine have been proposed. See, Decina et al., Biol. Psychiatry 28:502 (1990); Wagner et al., Pharmacopsychiatry 21:301 (1988); Pomerleau et al., Addictive Behaviors 9:265 (1984); Onaivi et al., Life Sci. 54(3):193 (1994); Tripathi et al., JPET 221: 91–96 (1982); and Hamon, Trends in Pharmacol. Res. 15:36.

Various nicotinic compounds have been reported as being useful for treating a wide variety of conditions and disorders. See, for example, Williams et al. DN&P 7(4):205–227 (1994), Arneric et al., CNS Drug Rev. 1(1):1–26 (1995), Arneric et al., Exp. Opin. Invest. Drugs 5(1):79–100 (1996), Bencherif et al., JPET 279:1413 (1996), Cosford et al., J. Med. Chem. 39: 3235–3237 (1996), Lippiello et al., JPET 279:1422 (1996), Damaj et al., Neuroscience (1997), Holladay et al., J. Med. Chem. 40 (28): 4169–4194 (1997), Bannon et al., Science 279: 77–80 (1998), PCT WO 94/08992, PCT WO 96/31475, and U.S. Pat. Nos. 5,583,140 to Bencherif et al., 5,597,919 to Dull et al., and 5,604,231 to Smith et al. Nicotinic compounds are reported as being particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic abnormality, a dopaminergic abnormality, an adrenergic abnormality and/or a serotonergic abnormality. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia, Tourette's syndrome and neuroendocrine disorders (e.g., obesity, bulemia and diabetes insipidus).

Nicotinic receptor antagonists have been used for the treatment of certain disorders. For example, mecamylamine has been marketed as Inversine by Merck & Co. Inc. as an antihypertensive agent; and trimethaphan has been marketed as Arfonad by Roche Laboratories as a vasodepressor agent. See, Goodman and Gilman's The Pharmacological Basis of Therapeutics, $6^{th}$ Ed p. 217 (1980). Nicotinic receptors have been implicated in convulsions, such as those that occur as a result of autosomal dominant nocturnal frontal lobe epilepsy. See, Steinlein et al., Nat. Genet. 11: 201–203 (1996). Nicotinic antagonists have been reported to inhibit viral infection. For example, nicotinic antagonists have been reported to inhibit the infection of dorsal root ganglion neurons by the rabies virus. See, Castellanos et al., Neurosci. Lett. 229: 198–200 (1997). Other uses for nicotinic antagonists have been proposed. See, for example, Popik et al., JPET 275: 753–760 (1995) and Rose et al., Clin. Pharm. Ther. 56(1): 86–9 (1994).

Nicotinic receptor ligands that interact with the alpha 7 receptor subtype have been proposed to be useful in the treatment of schizophrenia. There are a decreased number of hippocampal nicotinic receptors in postmortem brain tissue of schizophrenic patients. Also, there is improved psychological affect in smoking versus non-smoking schizophrenic patients. Nicotine improves sensory gating deficits in animals and schizophrenics. Blockade of the alpha 7 nicotinic receptor subtype induces a gating deficit similar to that seen in schizophrenia. See, Leonard et al., Schizophrenia Bulletin 22(3): 43145 (1996). Biochemical, molecular, and genetic studies of sensory processing in patients with the P50 auditory-evoked potential gating deficit suggest that the alpha 7 nicotinic receptor subtype may function in an inhibitory neuronal pathway. See, Freedman et al., Biological Psychiatry 38(1):22–33 (1995).

It would be desirable to provide a useful method for the prevention and treatment of a condition or disorder by administering a nicotinic compound to a patient susceptible to or suffering from such a disorder. It would be highly beneficial to provide individuals suffering from certain disorders with interruption of the symptoms of those disorders by the administration of a pharmaceutical composition containing an active ingredient having nicotinic pharmacology and providing a beneficial effect, but which does not provide any significant associated side effects (e.g., increased heart rate and blood pressure attendant with interaction of that compound with cardiovascular sites). It would be highly desirable to provide a pharmaceutical composition incorporating a compound that interacts with nicotinic receptors, but which composition does not significantly effect those receptor subtypes which have the potential to induce undesirable side effects (e.g., appreciable cardiovascular effects and appreciable activity at skeletal muscle sites).

SUMMARY OF THE INVENTION

The present invention relates to carbon-linked aromatic azabicyclo compounds, and in particular, aromatic alkylene azabicyclo compounds, aromatic alkyl azabicyclo compounds and oxacyclic alkyl azabicyclo compounds. Representative compounds are 2-((3-pyridyl)methyl)-1-azabicyclo[2.2.2]octane, 2-((3-pyridyl)methyl)-1-azabicyclo[2.2.2]octan-3-one, 2-((3-pyridyl)methylene)-1-azabicyclo[2.2.2]octane and 2-((3-pyridyl)methyl)-1-azabicyclo[2.2.2]octan-3-ol, 2-((3-oxolanyl)methyl)-1-azabicyclo[2.2.2]octan-3-one.

The present invention also relates to methods for synthesizing those types of compounds. The present invention also relates to prodrug derivatives of the compounds of the present invention.

Compounds of the present invention exhibit activity at acetylcholine receptors and are useful towards modulating release of ligands involved in neurotransmission. Compounds of the present invention are selective to certain nicotinic acetylcholine receptor subtypes, and can act as antagonists at those receptor subtypes. Hence, the present invention relates to methods for modulating the activity of certain nicotinic acetylcholine receptor subtypes by administering a compound of the present invention.

The present invention also relates to methods for the prevention or treatment of conditions and disorders. The present invention also relates to methods for the prevention or treatment of conditions and disorders, including central nervous system (CNS) disorders, which are characterized by an alteration in normal neurotransmitter release. The methods involve administering to a subject an effective amount of a compound of the present invention.

The present invention, in another aspect, relates to a pharmaceutical composition comprising an effective amount of a compound of the present invention. Such a pharmaceutical composition incorporates a compound that, when employed in effective amounts, has the capability of interacting with relevant nicotinic receptor sites of a subject, and hence has the capability of acting as a therapeutic agent in the prevention or treatment of disorders characterized by an alteration in normal neurotransmitter release. Preferred pharmaceutical compositions comprise novel compounds of the present invention.

The compounds of the present invention are beneficial in therapeutic applications requiring a selective inhibition at certain nicotinic receptor subtypes; that is, the compounds are antagonists at certain nicotinic receptor subtypes. The pharmaceutical compositions of the present invention are useful for the prevention and treatment of a wide variety of conditions or disorders. The compounds of the present invention are useful for treating certain CNS conditions and disorders; such as in providing neuroprotection, in treating patients susceptible to convulsions, in treating depression, in treating autism, in treating certain neuroendocrine disorders, and in the management of stroke. The compounds of the present invention also are useful in treating hypertension, for effecting weight loss, in treating type II diabetes and neoplasia, or as anti-bacterial or antiviral agents. The compounds of the present invention also are useful, when appropriately radio-labeled, as probes in life science applications (e.g., as selective probes in neuroimaging applications).

The pharmaceutical compositions provide therapeutic benefit to individuals suffering from such conditions or disorders and exhibiting clinical manifestations of such conditions or disorders, in that the compounds within those compositions, when employed in effective amounts, have the potential to (i) exhibit nicotinic pharmacology and affect relevant nicotinic receptors sites (e.g., act as a pharmacological antagonists at nicotinic receptors), and (ii) modulate neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts, not cause appreciable adverse side effects (e.g., significant increases in blood pressure and heart rate, significant negative effects upon the gastrointestinal tract, and significant effects upon skeletal muscle). The pharmaceutical compositions of the present invention are believed to be safe and effective with regards to prevention and treatment of various conditions or disorders.

The foregoing and other aspects of the present invention are explained in detail in the detailed description and examples set forth below.

DETAILED DESCRIPTION OF THE INVENTION

The compounds of the present invention include compounds of the formula:

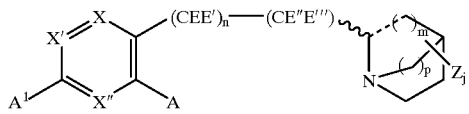

where the wavy line in the structure indicates that the bond can be a C—C or C=C bond; the dashed line in the structure indicates that the bond can be a C—C or C=C bond; and at least one of the wavy or dashed lines is a C—C bond; X, $X^I$ and $X^{II}$ are individually nitrogen or carbon bonded to a species hereinafter defined as $A^{II}$. A, $A^I$ and $A^{II}$ are individually substituent species characterized as having a sigma m value greater than 0, often greater than 0.1, and generally greater than 0.2, and even greater than 0.3; less than 0 and generally less than −0.1; or 0; as determined in accordance with Hansch et al., Chem. Rev. 91:165 (1991) (but preferably, each substituent species has a sigma m value which is between about −0.3 and about 0.75, and frequently is between about −0.25 and about 0.6, and each individual substituent species can have a sigma m value of 0); n is an integer from 0 to 3, preferably 0, 1 or 2, and more preferably 0 or 1, and most preferably 0; m is 0, 1 or 2, preferably 1; p is 1 or 2 preferably 2; E, $E^I$, $E^{II}$ and $E^{III}$ individually represent hydrogen, alkyl (e.g., straight chain or branched alkyl including $C_1-C_8$, preferably $C_1-C_5$, such as methyl, ethyl, or isopropyl), substituted alkyl, halo substituted alkyl (e.g., straight chain or branched alkyl including $C_1-C_8$, preferably $C_1-C_5$, such as trifluoromethyl or trichloromethyl), cycloalkyl, substituted cycloalkyl, cycloalkenyl, substituted cycloalkenyl, heterocyclyl, substituted heterocyclyl, aryl, substituted aryl, alkylaryl, substituted alkylaryl, arylalkyl or substituted arylalkyl; all of E, $E^I$, $E^{II}$, $E^{III}$ can be hydrogen, or at least one of E, $E^I$, $E^{II}$, $E^{III}$ is non-hydrogen (e.g., alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl) and the remaining E, $E^I$, $E^{II}$, $E^{III}$ are hydrogen; either E and $E^I$ or $E^{II}$ and $E^{III}$ and their associated carbon atom can combine to form a ring structure such as cyclopentyl, cyclohexyl or cycloheptyl; either E and $E^{II}$ or $E^I$ and $E^{III}$ and their associated carbon atoms can combine to form a ring structure such as cyclopentyl, cyclohexyl or cycloheptyl; j is an integer from 0 to 3, preferably 0 or 1; Z represents a non-hydrogen substituent, such as alkyl (e.g., straight chain or branched alkyl including $C_1$–$C_8$, preferably $C_1$–$C_5$, such as methyl, ethyl, or isopropyl), substituted alkyl, acyl, hydroxy, alkoxy, alkoxycarbonyl or aryloxycarbonyl, or oxygen (e.g., thereby forming a carbonyl functionality). More specifically, A and $A^I$ include H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, OH, CN, $NO_2$, $C_2R'$, SH, SR', $N_3$, $SO_2R'$, OR', $(CR'R")_qOR'$, O—$(CR'R")_q$ $C_2R'$, SR', C(=O)NR'R", NR'C(=O)R", C(=O)R', $(CR'R")_qC_2R'$, C(=O)OR', OC(=O)R', OC(=O)NR'R" and NR'C(=O)OR" where q is an integer from 1 to 6 and R' and R" are individually hydrogen or alkyl (e.g., $C_1$–$C_{10}$ alkyl, preferably $C_1$–$C_5$ alkyl, and more preferably methyl, ethyl, isopropyl or isobutyl), cycloalkyl (e.g., cyclopropyl, cyclobutyl, cyclopentyl, cyclohexyl, cycloheptyl, and adamantyl), a non-aromatic heterocyclic ring wherein the heteroatom of the heterocyclic moiety is separated from any other nitrogen, oxygen or sulfur atom by at least two carbon atoms (e.g., quinuclidinyl, pyrrolidinyl, and piperidinyl), an aromatic group-containing species (e.g., pyridyl, quinolinyl, pyrimidinyl, furanyl, phenyl, and benzyl where any of the foregoing can be suitably substituted with at least one substituent group, such as alkyl, alkoxyl, halo, or amino substituents). Other representative aromatic ring systems are set forth in Gibson et al., *J. Med. Chem.* 39:4065 (1996). Typically, $X^{II}$ is nitrogen or carbon bonded to $A^{II}$, where $A^{II}$ most preferably includes NR'R", OR' and $NO_2$, where R' and R" are as defined hereinbefore. Typically, $A^{II}$ is $NH_2$, $NHCH_3$ or $N(CH_3)_2$, with $NH_2$ being most preferred. Preferably, when $X_{II}$ is carbon bonded to $A^{II}$, $A^I$ is not a substituent bonded to the carbon of the ring (as shown in the structure) through an oxygen atom. Typically, X is carbon bonded to $A^{II}$, preferably hydrogen.

Typically, $X^I$ is nitrogen or carbon bonded to $A^{II}$. Either $A^I$ and a substituent of $X^I$ or $A^I$ and a substituent of $X^{II}$ can combine to form one or more saturated or unsaturated, substituted or unsubstituted carbocyclic or heterocyclic rings containing, but not limited to, ether, acetal, thioether, thioester, ketal, amine, ketone, lactone, lactam, carbamate, or urea functionalities. In addition, it is highly preferred that A is hydrogen and it is preferred that $A^I$ is hydrogen. Preferably, E, $E^I$ and $E^{II}$ are hydrogen. In one preferred embodiment, n is 1 or 2, E, $E^I$ and $E^{II}$ each are hydrogen, and $E^{III}$ is alkyl (e.g., methyl) or akylaryl. In another preferred embodiment, n is 1 or 2 and E, $E^I$, $E^{II}$, $E^{III}$ each are hydrogen. Depending upon the identity and positioning of each individual E, $E^I$, $E^{II}$ and $E^{III}$, certain compounds can be optically active, and/or can exist in the E or Z form. Additionally, compounds of the present invention can have chiral centers within the side chain (e.g., the compound can have an R or S configuration). Depending upon E, $E^I$, $E^{II}$ and $E^{III}$, compounds of the present invention have chiral centers, and the present invention relates to racemic mixtures of such compounds as well as single enantiomers. Typically, the selection of n, E, $E^I$, $E^{II}$ and $E^{III}$ is such that up to about 4, and frequently up to 3, and usually 0, 1 or 2, of the substituents designated as E, $E^I$, $E^{II}$ and $E^{III}$ are non-hydrogen substituents (i.e., substituents such as alkyl or halo-substituted alkyl). Typically, when $X^{II}$ is N, it is preferred that $A^I$ is H, Br or OR' (where R' preferably is methyl, ethyl, isopropyl, isobutyl or tertiary butyl).

As employed herein, "alkyl" refers to straight chain or branched alkyl radicals including $C_1$–$C_8$, preferably $C_1$–$C_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent groups as defined above; "cycloalkyl" and "cycloalkenyl" refer to saturated or unsaturated cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above; "acyl" refers to straight chain or branched alkyl-, alkenyl-, or substituted alkyl-carbonyl radicals including $C_1$–$C_8$, preferably $C_1$–$C_5$, such as formyl, acetyl, or propanoyl; "alkoxycarbonyl" refers to an alkyl or substituted alkyl radical attached to an O-carbonyl moiety; and "aryloxycarbonyl" refers to an aryl or substituted aryl radical attached to an O-carbonyl moiety.

Certain preferred compounds of the present invention can be represented by the formula:

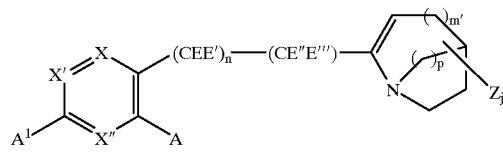

where X, $X^I$, $X^{II}$, A, $A^I$, E, $E^I$, $E^{II}$, $E^{III}$, n, p, m, j and Z are as defined hereinbefore.

Certain other preferred compound of the present invention can be represented by the formula:

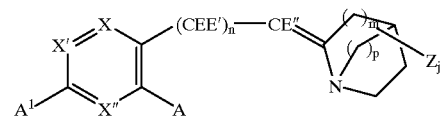

where X, $X^I$, $X^{II}$, A, $A^I$, E, $E^I$, $E^{II}$, n, p, m, j and Z are as defined hereinbefore. Such compounds can have both E and Z forms, can be synthesized as isomeric mixtures, and can be separated into pure enantiomers by techniques such as chromographic techniques.

Certain other preferred compounds of the present invention can be represented by the formula:

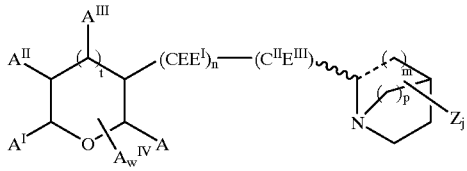

where A, A', A'', A''', E, E', E'', E''', n, p, m, j and Z are as defined hereinbefore; and t is 0,1 or 2, usually 0 or 1; w is an integer from 0 to 3, preferably 0 or 1; $A^{IV}$ represents a non-hydrogen substitutent, including alkyl, substituted alkyl, alkenyl, substituted alkenyl, heterocyclyl, substituted heterocyclyl, cycloalkenyl, substituted cycloalkenyl, cycloalkyl, substituted cycloalkyl, aryl, substituted aryl, alkylaryl, substituted alkylaryl, arylalkyl, substituted arylalkyl, F, Cl, Br, 1, NR'R'', $CF_3$, OH, CN, $NO_2$, $C_2R'$, SH, SR', $N_3$, $SO_2R'$, OR', $(CR'R'')_qOR'$, O—$(CR'R'')_qC_2R'$, SR', C(=O)NR'R'', NR'C(=O)R'', C(=O)R', $(CR'R'')_qC_2R'$, C(=O)OR', OC(=O)R', OC(=O)NR'R'' and NR'C(=O)OR' where q is an integer from 1 to 6 and R' and R'' are individually hydrogen or alkyl (e.g., $C_1$–$C_{10}$ alkyl, preferably $C_1$–$C_5$ alkyl, and more preferably methyl, ethyl, isopropyl or isobutyl), cycloalkyl or cycloalkenyl (e.g., cyclopropyl, cyclobutyl, cyclopentyl, cyclohexyl, cycloheptyl, and adamantyl).

Representative compounds of the present invention are as follows:
2-((3-pyridyl)methyl)-1-azabicyclo[2.2.2]octane
2-((5-bromo-3-pyridyl)methyl)-1-azabicyclo[2.2.2]octane
2-((5-amino-3-pyridyl)methyl)-1-azabicyclo[2.2.2]octane
2-((5-methoxy-3-pyridyl)methyl)-1-azabicyclo[2.2.2]octane
2-((5-ethoxy-3-pyridyl)methyl)-1-azabicyclo[2.2.2]octane
2-((5-isopropoxy-3-pyridyl)methyl)-1-azabicyclo[2.2.2]octane
2-((5-tert-butoxy-3-pyridyl)methyl)-1-azabicyclo[2.2.2]octane
2-((5-benzyloxy-3-pyridyl)methyl)-1-azabicyclo[2.2.2]octane
2-((5-hydroxy-3-pyridyl)methyl)-1-azabicyclo[22.2]octane
2-((5-ethynyl-3-pyridyl)methyl)-1-azabicyclo[2.2.2]octane
2-((5-cyano-3-pyridyl)methyl)-1-azabicyclo[2.2.2]octane
2-((6-methyl-3-pyridyl)methyl)-1-azabicyclo[2.2.2]octane
2-((6-fluoro-3-pyridyl)methyl)-1-azabicyclo[2.2.2]octane
2-((6-chloro-3-pyridyl)methyl)-1-azabicyclo[2.2.2]octane
2-((6-bromo-3-pyridyl)methyl)-1-azabicyclo[2.2.23]octane
2-((6-iodo-3-pyridyl)methyl)-1-azabicyclo[2.2.2]octane
2-((3-aminophenyl)methyl)-1-azabicyclo[2.2.2]octane
2-((3-pyridyl)methylene)-1-azabicyclo[2.2.2]octane
2-((5-methoxy-3-pyridyl)methylene)-1-azabicyclo[2.2.2]octane
2-((5-ethoxy-3-pyridyl)methylene)-1-azabicyclo[2.2.2]octane
2-((5-isopropoxy-3-pyridyl)methylene)-1-azabicyclo[2.2.2]octane
2-((5-tert-butoxy-3-pyridyl)methylene)-1-azabicyclo[2.2.2]octane
2-((5-benzyloxy-3-pyridyl)methylene)-1-azabicyclo[2.2.2]octane
2-(1-phenyl-1-(3-pyridyl)methyl)-1-azabicyclo[2.2.2]ctane
2-(2-phenyl-1-(3-pyridyl)ethyl)-1-azabicyclo[2.2.2]octane
2-(3-phenyl-1-(3-pyridyl)propyl)-1-azabicyclo[2.2.2]octane
2-(3-pyridyl)methyl)-1-azabicyclo[2.2.2]oct-2-ene
2-((5-methoxy-3-pyridyl)methyl)-1-azabicyclo[2.2.2]oct-2-ene
2-((5-ethoxy-3-pyridyl)methyl)-1-azabicyclo[2.2.2]oct-2-ene
2-((5-isopropoxy-3-pyridyl)methyl)-1-azabicyclo[2.2.2]oct-2-ene
2-((5-tert-butoxy-3-pyridyl)methyl)-1-azabicyclo[2.2.2]oct-2-ene
2-((5-benzyloxy-3-pyridyl)methyl)-1-azabicyclo[2.2.2]oct-2-ene
3-(phenyloxy)-2-3-pyridylmethyl)-1-azabicyclo[2.2.2]octane
3-(phenylmethoxy)-2-(3-pyridylmethyl)-1-azabicyclo[2.2.2]octane
3-((2-phenyl)ethoxy)-2-(3-pyridylmethyl)-1-azabicyclo[2.2.2]octane
2-((3-pyridyl)methyl)-1-azabicyclo[2.2.1]heptane
2-((5-methoxy-3-pyridyl)methyl)-1-azabicyclo[2.2.1]heptane
2-((5-ethoxy-3-pyridyl)methyl)-1-azabicyclo[2.2.1]heptane
2-((5-isopropoxy-3-pyridyl)methyl)1-azabicyclo[2.2.1]heptane
2-((5-tert-butoxy-3-pyridyl)methyl)-1-azabicyclo[2.2.1]heptane
2-((5-benzyloxy-3-pyridyl)methyl)-1-azabicyclo[2.2.1]heptane
2-((3-pyridyl) methylene)-1-azabicyclo[2.2.1]heptane
2-((5-methoxy-3-pyridyl)methylene)-1-azabicyclo[2.2.1]heptane
2-((5-ethoxy-3-pyridyl)methylene)-1-azabicyclo[2.2.1]heptane
2-((5-isopropoxy-3-pyridyl)methylene)-1-azabicyclo[2.2.1]heptane
2-((5-tert-butoxy-3-pyridyl)methylene)-1-azabicyclo[2.2.1]heptane
2-((5-benzyloxy-3-pyridyl)methylene)-1-azabicyclo[2.2.1]heptane
2-((3- pyridyl)methyl)-1-azabicyclo[3.2.1]octane
2-((5-methoxy-3-pyridyl)methyl)-1-azabicyclo[3.2.1]octane
2-((5-ethoxy-3-pyridyl)methyl)-1-azabicyclo[3.2.1]octane
2-((5-isopropoxy-3-pyridyl)methyl)-1-azabicyclo[3.2.1]octane
2-((5-tert-butoxy-3-pyridyl)methyl)-1-azabicyclo[3.2.1]octane
2-((5-benzyloxy-3-pyridyl)methyl)-1-azabicyclo[3.2.1]octane
2-((3-pyridyl)methylene)-1-azabicyclo[3.2.1]octane
2-((5-methoxy-3-pyridyl)methylene)-1-azabicyclo[3.2.1]octane
2-((5-ethoxy-3-pyridyl)methylene)-1-azabicyclo[3.2.1]octane
2-((5-isopropoxy-3-pyridyl)methylene)-1-azabicyclo[3.2.1]octane
2-((5-tert-butoxy-3-pyridyl)methylene)-1-azabicyclo[3.2.1]octane
2-((5-benzyloxy-3-pyridyl)methylene)1-azabicyclo[3.2.1]octane Other representative compounds of the present invention include:
2-(2-(3-pyridyl)ethyl)-1-azabicyclo[2.2.2]octane
2-(2-(3-pyridyl)ethyl)-1-azabicyclo[2.2.2]octan-3-one
2-(2-(3-pyridyl)ethyl)-1-azabicyclo[2.2.2]octan-3-ol
2-(2-(3-pyridyl)ethylene)-1-azabicyclo[2.2.2]octane
2-(2-(3-pyridyl)ethyl)-1-azabicyclo[2.2.2]oct-2-ene
2-(3-(3-pyridyl)propyl)-1-azabicyclo[2.2.2]octane
2-(3-(3-pyridyl)propylene)-1-azabicyclo[2.2.2]octane 2-(3-(3-pyridyl)propyl)-1-azabicyclo[2.2.2]oct-2-ene
2-(4-(3-pyridyl)butyl)-1-azabicyclo[2.2.2]octane
2-(4-(3-pyridyl)butylene)-1-azabicyclo[2.2.2]octane
2-(4-(3-pyridyl)butyl)-1-azabicyclo[2.2.2]oct-2-ene
2-((3-pyridyl)methyl)-1-azabicyclo[2.2.2]octan-3-ol
2-((3-pyridyl)methyl)-1-azabicyclo[2.2.2]octan-3-one
2-((3-pyridyl)methylene)-1-azabicyclo[2.2.2]octan-3-ol
2-((3-pyridyl)methylene)-1-azabicyclo[2.2.2]octan-3-one
2-(1-phenyl-1-(3-pyridyl)methyl)-1-azabicyclo[2.2.2]octan-3-ol
2-(2-phenyl-1-(3-pyridyl)ethyl)-1-azabicyclo[2.2.2]octan-3-ol
2-(3-phenyl-1-(3-pyridyl)propyl)-1-azabicyclo[2.2.2]octan-3-ol
2-(1-phenyl-1-(3-pyridyl)methyl)-1-azabicyclo[2.2.2]octan-3-one
2-(2-phenyl-1-(3-pyridyl)ethyl)-1-azabicyclo[2.2.2]octan-3-one
2-(3-phenyl-1-(3-pyridyl)propyl)-1-azabicyclo[2.2.2]octan-3-one
2-((3-pyridyl)methyl)-1-azabicyclo [2.2.1a]heptan-3-ol
2-((3-pyridyl)methyl)-1-azabicyclo[2.2.1]heptan-3-one
2-((3-pyridyl)methylene)-1-azabicyclo[2.2.1]heptan-3-ol
2-((3-pyridyl)methylene)-1-azabicyclo[2.2.1]heptan-3-one
2-((3-pyridyl)methyl)-1-azabicyclo[3.2.1]octan-3-ol
2-((3-pyridyl)methyl)-1-azabicyclo[3.2.1]octan-3-one
2-((3-pyridyl)methylene)-1-azabicyclo[3.2.1]octan-3-ol
2-((3-pyridyl)methylene)-1-azabicyclo[3.2.1]octan-3-one
2-((3-furyl)methylene)-1-azabicyclo[2.2.2]octane
2-((3-furyl)methyl)-1-azabicyclo[2.2.2]octane
2-((3-oxolanyl)methylene)-1-azabicyclo[2.2.1]octane
2-((4-methoxy-3-oxolanyl)methylene)-1-azabicyclo[2.2.2]octane
2-((4-ethoxy-3-oxolanyl)methylene)-1-azabicyclo[2.2.2]octane
2-((4-isopropoxy-3-oxolanyl)methylene)-1-azabicyclo[2.2.2]octane
2-((4-benzyloxy-3-oxolanyl)methylene)-1-azabicyclo[2.2.2]octane
2-((3-oxolanyl)methyl)-1-azabicyclo[2.2.2]octane
2-((4-methoxy-3-oxolanyl)methyl)-1-azabicyclo[2.2.2]octane
2-((4-ethoxy-3-oxolanyl)methyl)-1-azabicyclo[2.2.2]octane
2-((4-isopropoxy-3-oxolanyl)methyl)-1-azabicyclo[2.2.2]octane
2-((4-benzyloxy-3-oxolanyl)methyl)-1-azabicyclo[2.2.2]octane The manner in which 2-(3-(4-, 5-, and 6-substituted)pyridylmethyl)-1-azabicyclo[2.2.2]octanes of the present invention can be synthesized can vary. For example, 5-bromopyridine-3-carboxaldehyde and quinuclidin-3-one hydrochloride (commercially available from Aldrich), are reacted together in the presence of methanolic potassium hydroxide as described in Neilsen and Houlihan, Org. React. 16: 1–438 (1968). This aldol condensation product, 2-(3-(5-bromo)pyridylmethylene)-1-azabicyclo[2.2.2]octan-3-one, is then treated with sodium borohydride to yield the alcohol, 2-(3-(5-bromo)pyridylmethylene)-1-azabicyclo[2.2.2]octan-3-ol as a crystalline solid. This intermediate is reacted with neat thionyl chloride at room temperature to give 3-chloro-2-(3-(5-bromo)pyridylmethylene)-1-azabicyclo[2.2.2]octane as a pure crystalline solid. Reductive removal of the chlorine is accomplished by lithium trimethoxyaluminum hydride and copper iodide as described by Masamune et al., J. Am. Chem. Soc. 95: 6452 (1973) to give the desired product, 2-(3-(5-bromo)pyridylmethylene)-1-azabicyclo[2.2.2]octane, as a crystalline solid. This methylene intermediate can the be converted to the desired product, 2-(3-(5-bromo)pyridylmethyl)-1-azabicyclo[2.2.2]octane, by hydrogenation in the presence of palladium catalyst. Reaction conditions are controlled to avoid removal of the bromine substituent. The isomeric compounds, 2-(3-(4-bromo)pyridylmethyl)-1-azabicyclo[2.2.2]octane and 2-(3-(6-bromo)pyridylmethyl)-azabicyclo[2.2.2]octane can be prepared in a similar manner by replacing 5-bromopyridine-3-carboxaldehyde with 4-bromopyridine-3-carboxaldehyde or 6-bromopyridine-3-carboxaldehyde, respectively, in the synthetic approach given above.

The required aldehyde, 5-bromopyridine-3-carboxaldehyde, can be prepared from 5-bromonicotinic acid (commercially available from Aldrich Chemical Company and Lancaster Synthesis, Inc.). The 5-bromonicotinic acid can be treated with ethyl chloroformate producing the mixed anhydride, which can be reduced with lithium aluminum hydride in tetrahydrofuran (THF) at −78° C., to afford 5-bromo-3-hydroxymethylpyridine, as reported by A. Ashimori et al., Chem. Pharm. Bull. 38(9): 2446–2458 (1990). Alternatively, the 5-bromonicotinic acid can be esterified in the presence of sulfuric acid and ethanol, and the intermediate ethyl ester can be reduced with an excess of sodium borohydride to yield 5-bromo-3-hydroxymethylpyridine, according to the techniques reported in C. F. Nutaitis et al., Org. Prep. and Proc. Int. 24:143–146 (1992). The resulting 5-bromo-3-hydroxymethylpyridine can then be converted to 5-bromo-3-pyridinecarboxaldehyde by Swern oxidation using oxalyl chloride and dimethylsulfoxide according to the methods of M. J. Stocks et al., Tetrahedron Lett. 36(36): 6555–6558 (1995) and A. J. Mancuso et al., J. Org Chem. 44(23): 4148–4150 (1979). The aldehyde, 4-bromopyridine-3-carboxaldehyde can be synthesized according to methodology described by Chin et al. PCT WO 94/29893 or by methodology described by Ojea et al., Synlett. 6: 622–624 (1995). 6-Bromopyridine-3-carboxaldehyde can be prepared according to procedures described in Windschief and Voegtle, Synthesis 1: 87–92 (1994) or Fey et al German Patent No. 93/4320432.

The manner in which E and Z isomers of 2-(3-(4-, 5-, and 6-substituted)pyridylmethylene)-1-azabicyclo[2.2.2]octanes of the present invention can be synthesized can vary. For example, 5-bromopyridine-3-carboxaldehyde and quinuclidin-3-one hydrochloride (commercially available from Aldrich) are reacted together in the presence of methanolic potassium hydroxide as described in Neilsen and Houlihan, Org. React. 16: 1–438 (1968). This aldol condensation product, 2-(3-(5-bromo)pyridylmethylene)1-azabicyclo[2.2.2]octan-3-one, is then treated with sodium borohydride to yield the alcohol, 2-(3-(5-bromo)pyridylmethylene)-1-azabicyclo[2.2.2]octan-3-ol as a crystalline solid. This intermediate is reacted with neat thionyl chloride at room temperature to give 3-chloro-2-(3-(5-bromo)pyridylmethylene)-1-azabicyclo[2.2.2]octane as a crystalline solid. Reductive removal of the chlorine is accomplished by lithium trimethoxyaluminum hydride and copper iodide as described by Masamune et al., J. Am. Chem. Soc. 95: 6452 (1973) to give the desired product, 2-(3-(5-bromo)pyridylmethylene)-1-azabicyclo[2.2.2]octane. The isomeric compounds, 2-(3-(4-bromo)pyridylmethylene)-1-azabicyclo[2.2.2]octane and 2-(3-(6-bromo)pyridylmethylene)-1-azabicyclo[2.2.2]octane can be prepared in a similar manner by replacing 5-bromopyridine-3-carboxaldehyde with 4-bromopyridine-3-carboxaldehyde or 6-bromopyridine-3-carboxaldehyde, respectively, in the synthetic approach given above.

The manner in which 2-[(3-aminophenyl)methyl]-1-azabicyclo[2.2.2]octane is synthesized can vary. For example, in one method, 3-nitrobenzaldehyde can be condensed with 3-quinuclidinone in an aldol reaction using potassium hydroxide and ethanol to yield 2-[(3-nitrophenyl) methylene]-1-azabicyclo[2.2.2]octan-3-one. The latter compound can be converted to the corresponding dithioketal by treatment with 1,2-ethanedithiol and boron triflouride etherate. Reduction and desulfurization can be effected by hydrogenation using Raney nickel to yield 2-[(3-aminophenyl) methyl]-1-azabicyclo[2.2.2]octane. Alternatively, in another method, the aldol product, 2-[(3-nitrophenyl)methylene]-1-azabicyclo[2.2.2]octan-3-one can be reduced by treatment with sodium borohydride in methanol to give the alcohol, 2-[(3-nitrophenyl)methylene]-1-azabicyclo[2.2.2]octan-3-ol. The latter compound can be converted to the chloro intermediate, 3-chloro-2-[(3-nitrophenyl)methylene]-1-azabicyclo[2.2.2]octane dihydrochloride upon treatment with thionyl chloride. Dechlorination by hydrogenation with Raney nickel and carbon-carbon double bond reduction by hydrogenation over 10% palladium on carbon can then be effected to yield 2-[(3-aminophenyl)methyl]-1-azabicyclo[2.2.2]octane. Replacement of 3-nitrobenzaldehyde with 2-nitrobenzaldehyde or 4-nitrobenzaldehyde in the above synthetic approach affords the isomeric compounds, 2-[(2-aminophenyl)methyl]-1-azabicyclo[2.2.2]octane and 2-[(4-aminophenyl)methyl]-1-azabicyclo[2.2.2]octane, respectively.

The manner in which 2-[(2-, 3-, and 4-substituted phenyl) methyl]-1-azabicyclo[2.2.2]octanes are synthesized can vary. For example, in one method, 3-bromobenzaldehyde can be subjected to an aldol reaction with 3-quinuclidinone hydrochloride (commercially available from Aldrich Chemical Company) using potassium hydroxide in methanol to give 2-[(3-bromophenyl)methylene]-1-azabicyclo[2.2.2] octan-3-one. The latter unsaturated ketone can be reduced by hydrogenation using palladium over charcaol to give 2-[(3-bromophenyl)methyl]-1-azabicyclo[2.2.2]octan-3-one. Depending upon the choice of hydrogenation catalyst, it may be necessary to use suitable inhibitors to suppress dihologenation. For suitable catalysts and inhibitors, see Rylander, *Catalytic Hydrogenation in Organic Synthesis*, pp. 125–126 (1979). The resulting ketone can be reduced under Wolff-Kishner conditions with hydrazine and base (or under modified Wolff-Kishner conditions with tosylhydrazine and sodium cyanoborohydride) to yield 2-[(3-bromophenyl)methyl]-1-azabicyclo[2.2.2]octane. Methods similar to those described by A. D. Yanina et al., *Khim.-Farm. Zh.* 21(7):808–811 (1987) can be used. The isomeric compounds, 2-[(2-bromophenyl)methyl]-1-azabicyclo [2.2.2]octane and 2-[(4-bromophenyl)methyl]-1-azabicyclo [2.2.2]octane can be prepared in a similar manner by replacing 3-bromobenzaldehyde with 2-bromobenzaldehyde and 4-bromobenzaldehyde, respectively in the above synthetic approach. Alternatively, 2-[(3-bromophenyl)methyl]-1-azabicyclo[2.2.2]octane can be prepared form the previously described 2-[(3-aminophenyl)methyl]-1-azabicyclo[2.2.2] octane by conversion to the intermediate diazonium salt compound using sodium nitrite and acid at 0° C., followed by treatment with cuprous bromide under Sandmeyer reaction conditions. In a similar manner, 2-[(2-bromophenyl) methyl]-1-azabicyclo[2.2.2]octane and 2-[(4-bromophenyl) methyl]-1-azabicyclo[2.2.2]octane can be prepared from the corresponding amino compounds.

Compounds of the present invention may contain more than one carbon between the aromatic ring and azabicyclic ring functionalities. The manner in which such compounds as 2-(2-(3-pyridyl)ethyl)-1-azabicyclo[2.2.2]octane, 2-(2-(3-pyridyl)propyl)-1-azabicyclo[2.2.2]octane, and 2-(2-(3-pyridyl)butyl)-1-azabicyclo[2.2.2]octane of the present invention can be prepared can vary. For example, 2-(2-(3-pyridyl)ethyl)-1-azabicyclo[2.2.2]octane can be prepared by different methods. In one approach, 3-pyridineacetaldehyde (also known as 2-(3-pyridyl)ethanal) can be condensed with 3-quinuclidinone hydrochloride (commercially available from Aldrich Chemical Company) in a directed aldol reaction using a base such as potassium hydroxide or sodium hydroxide in methanol or sodium ethoxide in ethanol to afford 2-(2-(3-pyridyl)ethylene)-1-azabicyclo[2.2.2]octan-3-one. Aldol condensations between an aldehyde and a ketone with accompanying reaction modifications similar to those described by J. March, *Advanced Organic Chemistry, Reactions, Mechanisms, and Structure,* 2nd edition, pp.849–853 (1977) can be used to give a mixture of products. The carbon-carbon double bond of the resulting unsaturated ketone can be reduced by hydrogenation using palladium on charcoal to give the ketone, 2-(2-(3-pyridyl) ethyl)-1-azabicyclo[2.2.2]octan-3-one, which can be further reduced under Wolff-Kishner conditions to yield 2-(2-(3-pyridyl)ethyl)-1-azabicyclo[2.2.2]octane. Methods similar to those described by A. D. Yanina et al., *Khim.-Farm. Zh* 21(7): 808–811 (1987) can be used for the latter reductions. Alternatively, in another synthetic method, the carbonyl group of the above aldol product, 2-(2-(3-pyridyl)ethylene)-1-azabicyclo[2.2.2]octan-3-one can be reduced by treatment with sodium borohydride in methanol to give the alcohol, 2-(2-(3-pyridyl)ethylene)-1-azabicyclo[2.2.2]octan-3-ol. This alcohol can be converted to the chloro intermediate, 3-chloro-2-(2-(3-pyridyl)ethylene-1-azabicyclo[2.2.2] octane dihydrochloride upon treatment with thionyl chloride. Dechlorination can then be accomplished by hydrogenation with Raney nickel to afford 2-(2-(3-pyridyl) ethylene)-1-azabicyclo[2.2.2]octane dihydrochloride. The carbon-carbon double bond of the latter compound can then be reduced by hydrogenation over 10% palladium on charcoal in methanol to yield 2-(2-(3-pyridyl)ethyl)-1-azabicyclo[2.2.2]octane dihydrochloride.

Related compounds of the present invention such as 2-(2-(3-pyridyl)ethyl)-1-azabicyclo[2.2.2]octan-3-one can be prepared by reduction of the carbon-carbon double bond of the aldol reaction product, 2-(2-(3-pyridyl)ethylene)-1-azabicyclo[2.2.2]octan-3-one by hydrogenation over 10% palladium on charcoal in methanol. Also, 2-(2-(3-pyridyl) ethylene)-1-azabicyclo[2.2.2]octan-3-ol can be prepared by reducing the ketone functionality of 2-(2-(3-pyridyl)ethyl)-1-azabicyclo[2.2.2]octan-3-one with sodium borohydride in methanol. The latter alcohol can also be prepared by the hydrogenation of 2-(2-(3-pyridyl)ethylene)-1-azabicyclo [2.2.2]octan-3-one over Raney nickel in methanol.

Replacement of 2-(3-pyridyl)ethanal in the above synthetic approach with 2-(3-pyridyl)propanal leads to the following compounds: 2-(1-methyl-3-(3-pyridyl) propylene)-1-azabicyclo[2.2.2]octan-3-one, 2-(3-(3-pyridyl)propyl)-1-azabicyclo[2.2.2]octan-3-one, 2-(1-methyl-3-(3-pyridyl)propylene)-1-azabicyclo[2.2.2]octan-3-ol, 3-chloro-2-(1-methyl-3-(3-pyridyl)propylene)-1-azabicyclo[2.2.2]octane dihydrochloride, 2-(1-methyl-3-(3-pyridyl)propylene)-1-azabicyclo[2.2.2]octane dihydrochloride, and 2-(3-(3-pyridyl)propyl)-1-azabicyclo [2.2.2]octane. Also, 2-(3-(3-pyridyl)propyl)-1-azabicyclo [2.2.2]octan-3-one, and 2-(3-(3-pyridyl)propyl)-1-azabicyclo[2.2.2]octan-3-ol can be prepared by the previously described methods.

Replacement of 2-(3-pyridyl)ethanal in the above synthetic approach with 2-(3-pyridyl)butanal leads to the following compounds: 2-(1-methyl-4-(3-pyridyl)butylene)-1-azabicyclo[2.2.2]octan-3-one, 2-(4-(3-pyridyl)butyl)-1-azabicyclo[2.2.2]octan-3-one, 2-(1-methyl4-(3-pyridyl) butylene)-1-azabicyclo[2.2.2]octan-3-ol, 3-chloro-2-(1-methyl-4-(3-pyridyl)butylene)-1-azabicyclo[2.2.2]octane dihydrochloride, 2-(1-methyl-4-(3-pyridyl)butylene)-1-azabicyclo[2.2.2]octane dihydrochloride, and 2-(4-(3-pyridyl)butyl)-1-azabicyclo[2.2.2]octane. Also, 2-(4-(3-pyridyl)butyl)-1-azabicyclo[2.2.2]octan-3-one, and 2-(4-(3-pyridyl)butyl)-1-azabicyclo[2.2.2]octan-3-ol can be prepared by the previously described methods.

The requisite aldehyde for the above aldol condensation, 3-pyridineacetaldehyde (also known as 2-(3-pyridyl) ethanal) can be prepared by a number of synthetic methods. In one approach 3-pyridylacetic acid hydrochloride (commercially available from Aldrich Chemical Company and Lancaster Synthesis, Inc.) can be treated with trimethylsilyl chloride and triethylamine. The resulting trimethylsilyl ester can then be reduced with diisobutylaluminum hydride according to the method of S. Chandrasekhar et al., *Tetrahedron Lett.* 39: 909–910 (1998). Alternatively, 3-pyridineacetaldehyde can be prepared from 3-(3-pyridyl) acrylic acid (commercially available from Aldrich Chemical Company and Lancaster Synthesis, Inc.) using the method of D. H. Hey et al., *J. Chem. Soc. Part II:* 1678–1683 (1950). In this method, 3-(3-pyridyl)acrylic acid can be converted to its acid chloride by treatment with thionyl chloride. Subsequent treatment of the acid chloride with ammonia according to the method of L. Panizza, *Helv. Chim. Acta* 24: 24E–28E (1941) yields β-(3-pyridyl)acrylamide. Hofmann rearrangement of the latter amide by treatment with sodium hypochlorite affords methyl 2-(3-pyridyl)vinylcarbamate which can be hydrolyzed with refluxing 6N sulfuric acid in ethanol to give 3-pyridineacetaldehyde, which can be isolated as its 2,4-dinitrophenylhydrazone sulfate.

The aldehyde, 3-(3-pyridyl)propanal required for the preparation of 2-(3-(3-pyridyl)propyl)-1-azabicyclo[2.2.2] octane and related compounds can be prepared from 3-(3-pyridyl)propanol (commercially available from Aldrich Chemical Company and Lancaster Synthesis, Inc.). Oxidation of the latter alcohol with lead acetate in pyridine according to the method of S. J. Ratcliffe et al., *J. Chem. Soc., Perkin Trans.* 1 Issue 8: 1767–1771 (1985) affords 3-(3-pyridyl)propanal. Alternatively, 3-(3-pyridyl)propanal can be prepared by Swern oxidation of 3-(3-pyridyl) propanol using oxalyl chloride in dimethyl sulfoxide and dichloromethane according to the methods of M. J. Stocks et al., Tetrahedron Lett. 36(36): 6555–6558 (1995) and A. J. Mancuso et al., *J. Org. Chem.* 44(23): 4148–4150 (1979).

The aldehyde, 3-(3-pyridyl)butanal required for the preparation of 2-(4-(3-pyridyl)propyl)-1-azabicyclo[2.2.2] octane and related compounds can be prepared from 3-(3-pyridyl)propanol (commercially available from Aldrich Chemical Company and Lancaster Synthesis, Inc.) by a homologative process according to the method of G. Solladié et al., *Tetrahedron:Asymmetry* 8(5): 801–810 (1997). Treatment of 3-(3-pyridyl)propanol with tribromoimidazole and triphenylphosphine yields 1-bromo-3-(3-pyridyl) propane, which can be condensed with the lithium salt of 1,3-dithiane. Removal of the dithianyl group of the resulting compound with aqueous mercuric chloride and mercuric oxide affords 4-(3-pyridyl)butanal.

The manner in which 2-(1-phenyl-1-(3-pyridyl)methyl)-1-azabicyclo[2.2.2]octanes, 2-(2-phenyl-1-(3-pyridyl) ethyl)-1-azabicyclo[2.2.2]octanes and 2-(3-phenyl-1-(3-pyridyl)propyl)-1-azabicyclo[2.2.2]octanes of the present invention can be synthetically produced can vary. For example, pyridine-3-carboxaldehyde and quinuclidin-3-one hydrochloride (commercially available from Aldrich) are reacted together in the presence of methanolic potassium hydroxide as described in Neilsen and Houlihan, *Org. React.* 16: 14–38 (1968) to give the aldol condensation product, 2-(3-pyridylmethylene)-1-azabicyclo[2.2.2]octan-3-one as a crystalline solid. 2-(3-pyridylmethylene)-1-azabicyclo [2.2.2]octan-3-one can then be converted to 2-(1-phenyl-1-(3-pyridyl)methyl)-1-azabicyclo[2.2.2]octane-3-one by treatment with phenylmagnesium bromide in ethanol at −10° C. The ketone is then treated with sodium borohydride to yield the alcohol, 2-(1-phenyl-1-(3-pyridyl)methyl)-1-azabicyclo[2.2.2]octan-3-ol. This intermediate is reacted with neat thionyl chloride at room temperature to give 3-chloro-2-(1-phenyl-1-(3-pyridyl)methyl)-1-azabicyclo [2.2.2]octane as a crystalline solid. Removal of the chlorine is accomplished by hydrogenation in the presence of Raney nickel as described by de Koning, *Org. Prep. Proced Int.* 7:31 (1975) to give the desired product, 2-(1-phenyl-1-(3-pyridyl)methyl)-1-azabicyclo[2.2.2]octane. The related compounds, 2-(2-phenyl-1-(3-pyridyl)ethyl)-1-azabicyclo [2.2.2]octane and 2-(3-phenyl-1-(3-pyridyl)propyl)-1-azabicyclo[2.2.2]octane can be prepared in a similar manner by replacing phenylmagnesium bromide with benzylmagnesium bromide or 2-phenethylmagnesium bromide, respectively, in the synthetic approach given above.

The manner in which 2-(3-(4- , 5-, and 6-substituted) pyridylmethyl)-1-azabicyclo[2.2.2]oct-2-enes of the present invention can be synthesized can vary. For example, 5-bromopyridine-3-carboxaldehyde and quinuclidin-3-one hydrochloride (commercially available from Aldrich) are reacted together in the presence of methanolic potassium hydroxide as described in Neilsen and Houlihan, *Org. React.* 16: 1–438 (1968). This aldol condensation product, 2-(3-(5-bromo)pyridylmethylene)-1-azabicyclo[2.2.2]octan-3-one, is then dissolved in ethanol and hydrogenated with 5% palladium on charcoal to afford 2-(3-(5-bromo) pyridylmethyl)-1-azabicyclo[2.2.2]octan-3-one. Reaction conditions are controlled to avoid removal of the bromine substituent. Treatment with sodium borohydride gives the alcohol, 2-(3-(5-bromo)pyridylmethyl)-1-azabicyclo[2.2.2] octan-3-ol. This intermediate is reacted with neat thionyl chloride at room temperature to give 3-chloro-2-(3-(5-bromo)pyridylmethyl)-1-azabicyclo[2.2.2]octane. Elimination of the aliphatic chloro moiety is accomplished by treatment with 1,8-diazabicyclo[5.4.0]undec-7-ene, according to the method of Wolkoff, *J. Org. Chem.* 47: 1944–1946 (1982), to give the desired product, 2-(3-(5-bromo) pyridylmethyl)-1-azabicyclo[2.2.2]oct-2-ene. The isomeric compounds, 2-(3-(4-bromo)pyridylmethyl)-1-azabicyclo [2.2.2]oct-2-ene and 2-(3-(6-bromo)pyridylmethyl)-1-azabicyclo[2.2.2]oct-2-ene can be prepared in a similar manner by replacing 5-bromopyridine-3-carboxaldehyde with 4-bromopyridine-3-carboxaldehyde or 6-bromopyridine-3-carboxaldehyde, respectively, in the synthetic approach given above.

The manner in which 3-(phenyloxy)-2-(3-pyridylmethyl)-1-azabicyclo[2.2.2]octane of the present invention is synthesized can vary. For example, pyridine-3-carboxaldehyde and quinuclidin-3-one hydrochloride (commercially available from Aldrich) are reacted together in the presence of methanolic potassium hydroxide as described in Neilsen and Houlihan, *Org. React.* 16: 14–38 (1968). This aldol condensation product, 2-(3-pyridylmethylene)-1-azabicyclo[2.2.2] octan-3-one, is then dissolved in methanol and hydrogenated in the presence of Raney nickel catalyst to afford 2-(3-pyridylmethyl)-1-azabicyclo[2.2.2]octan-3-ol. This alcohol is then etherified with phenol via Mitsunobu coupling with diethylazidocarboxylate and triphenylphosphine, as described by Guthrie et al., *J. Chem. Soc., Perkin Trans I* 45: 2328 (1981), to afford the desired product, 3-(phenyloxy)-2-(3-pyridylmethyl)-1-azabicyclo[2.2.2]octane.

The manner in which 3-(phenylmethoxy and 2-phenylethoxy)-2-(3-pyridylmethyl)-1-azabicyclo[2.2.2] octanes of the present invention are synthesized can vary. For example, pyridine-3-carboxaldehyde and quinuclidin-3-one hydrochloride (commercially available from Aldrich) are reacted together in the presence of methanolic potassium hydroxide as described in Neilsen and Houlihan, *Org. React.* 16: 1–438 (1968). This aldol condensation product, 2-(3-pyridylmethylene)-1-azabicyclo[2.2.2]octan-3one, is then dissolved in methanol and hydrogenated in the presence of Raney nickel catalyst to afford 2-(3-pyridylmethyl)-1-azabicyclo[2.2.2]octan-3-ol. Treatment of the alcohol with sodium hydride followed by benzyl bromide in a suitable solvent affords the desired product, 3-(phenylmethoxy)-2-(3-pyridylmethyl)-azabicyclo[2.2.2]octane. 3-(2-Phenylethoxy)2-(3-pyridylmethyl)-1-azabicyclo[2.2.2] octane can be synthesized by substituting benzyl bromide with 2-bromoethylbenzene.

The manner in which 2-(3-(4-, 5-, and 6-substituted) pyridylmethyl)-1-azabicyclo[2.2]heptanes of the present invention can be synthesized can vary. For example, 5-bromopyridine-3-carboxaldehyde and 1-azabicyclo[2.2.1] heptan-3-one, which is itself synthesized according to the method of Wadsworth et al., U.S. Pat. No. 5,217,975, are reacted together in the presence of methanolic potassium hydroxide as described in Neilsen and Houlihan, *Org React.* 16: 1–438 (1968). This aldol condensation product, 2-(3-(5-bromo)pyridylmethylene)-1-azabicyclo[2.2.1]heptan-3-one, is then treated with sodium borohydride to yield the alcohol, 2-(3-(5-bromo)pyridylmethylene)-1-azabicyclo[2.2.1] heptan-3-ol as a crystalline solid. This intermediate is reacted with neat thionyl chloride at room temperature to give 3-chloro-2-(3-(5-bromo)pyridylmethylene)-1-azabicyclo[2.2.1]heptane. Reductive removal of the chlorine is accomplished by lithium trimethoxyaluminum hydride and copper iodide as described by Masamune et al., *J. Am. Chem. Soc.* 95: 6452 (1973) to give the desired product, 2-(3-(5-bromo)pyridylmethylene)-1-azabicyclo[2.2.1] heptane, as a crystalline solid. This methylene intermediate can the be converted to the desired product, 2-(3-(5-bromo) pyridylmethyl)-1-azabicyclo[2.2.1]heptane, by hydrogenation in the presence of palladium on charcoal catalyst. Reaction conditions are controlled to avoid removal of the bromine subtituent. The isomeric compounds, 2-(3-(4-bromo)pyridylmethyl)-1-azabicyclo[2.2.1]heptane and 2-(3-(6-bromo)pyridylmethyl)-1-azabicyclo[2.2.1]heptane can be prepared in a similar manner by replacing 5-bromopyridine-3-carboxaldehyde with 4-bromopyridine-3-carboxaldehyde or 6-bromopyridine-3-carboxaldehyde, respectively, in the synthetic approach given above.

The manner in which 2-(3-(4-, 5-, and 6substituted) pyridylmethyl)-1-azabicyclo[3.2.1]octanes of the present invention can be synthesized can vary. For example, 5-bromopyridine-3-carboxaldehyde and 1-azabicyclo[3.2.1] octan-3-one, which is itself synthesized according to the method of Thill and Aaron *J. Org. Chem.* 33: 4376–4379 (1969), are reacted together in the presence of methanolic potassium hydroxide as described in Neilsen and Houlihan, *Org. React.* 16: 1–438 (1968). The Aldol condensation products, 2-(3-(5-bromo)pyridylmethylene)-1-azabicyclo [3.2.1]octan-3-one and 4-(3-(5-bromo)pyridylmethylene)-1-azabicyclo[3.2.I]octan-3-one are then chromatographically separated. The desired 2-(3-(5-bromo)pyridylmethylene)-1-azabicyclo[3.2.1]octan-3-one, is then treated with sodium borohydride to yield the alcohol, 2-(3-(5-bromo) pyridylmethylene)-1-azabicyclo[3.2.1]octan-3-ol as a crystalline solid. This intermediate is reacted with neat thionyl chloride at room temperature to give 3-chloro-2-(3-(5-bromo)pyridylmethylene)-1-azabicyclo[3.2.1]octane dihydrochloride. Reductive removal of the chlorine is accomplished by lithium trimethoxyaluminum hydride and copper iodide as described by Masamune et al., *J. Am. Chem. Soc.* 95: 6452 (1973) to give, 2-(3-(5-bromo)pyridylmethylene)-1-azabicyclo[3.2.1]octane, as a crystalline solid. This methylene intermediate can then be converted to the final product, 2-(3-(5-bromo)pyridylmethyl)-1-azabicyclo[3.2.1] octane, by hydrogenation in the presence of palladium on charcoal catalyst. The isomeric compounds, 2-(3-(4-bromo) pyridylmethyl)-1-azabicyclo[3.2.1]octane and 2-(3-(6-bromo)pyridylmethyl)-1-azabicyclo[3.2.1]octane can be prepared in a similar manner by replacing 5-bromopyridine-3-carboxaldehyde with 4-bromopyridine-3-carboxaldehyde or 6-bromopyridine-3-carboxaldehyde, respectively, in the synthetic approach given above.

The manner in which 2-((5-bromo-3-pyridyl)methyl)-1-azabicyclo[2.2.2]octane and other analogous compounds possessing substituents at the C-5 position of the pyridine ring are synthesized can vary. In another example, 2-((5-bromo-3-pyridyl)methyl)-1-azabicyclo[2.2.2]octane can be prepared starting with the aldol condensation of 5-bromo-3-pyridinecarboxaldehyde and 3-quinuclidinone hydrochloride (commercially available from Aldrich Chemical Company) which proceeds in 75% yield using potassium hydroxide in methanol. The carbon-carbon double bond of the resulting 2-((5-bromo-3-pyridyl)methylene)-1-azabicyclo[2.2.2]octan-3-one can be selectively reduced with an appropriate reducing agent, such as lithium tri-sec-butylborohydride (L-Selectride®) or potassium tri-sec-butylborohydride (K-Selectride®) (available from Aldrich Chemical Company) in tetrahydrofuran at −78° C. using methodology described by J. M. Fortunato et al., *J Org. Chem.* 41 (12): 2194–2200 (1976) or with sodium borohydride modified with nickel(1) chloride hexahydrate in an ethanolic or aqueous solution to give 2-((5-bromo-3-pyridyl)methyl)-1-azabicyclo[2.2.2]octan-3-one. The latter ketone can be reduced under Wolff-Kishner conditions with hydrazine and base (or under modified Wolff-Kishner conditions with tosylhydrazine and sodium cyanoborohydride) to yield 2-((5-bromo-3-pyridyl)methyl)-1-azabicyclo[2.2.2] octane.

A number of compounds possessing substituents at the C-5 position of the pyridine ring can be prepared from 2-((5-bromo-3-pyridyl)methyl)-1-azabicyclo[2.2.2]octane. For example, the 5-amino-substituted compound can be prepared from the corresponding 5-bromo compound using ammonia in the presence of a copper catalyst according to the general method of C. Zwart et al., *Recueil Trav. Chim. Pays-Bas* 74: 1062–1069 (1955). 5-Alkylamino substituted compounds can be prepared in a similar manner. 5-Alkoxy substituted analogs can be prepared from the corresponding 5-bromo compounds by heating with a sodium alkoxide in N,N-dimethylformamide or by use of a copper catalyst according to the general techniques described in D. L. Comins et al., *J. Org. Chem.* 55: 69–73 (1990) and H. J. den Hertog et al., *Recl. Trav. Chim. Pays-Bas* 74: 1171–1178 (1955). 5-Ethynyl-substituted compounds can be prepared from the appropriate 5-bromo compounds by palladium catalyzed coupling using 2-methyl-3-butyn-2-ol, followed by base (sodium hydride) catalyzed deprotection according to the general techniques described in N. D. P. Cosford et al., *J. Med. Chem.* 39: 3235–3237 (1996). The 5-ethynyl analogs can be converted into the corresponding 5-ethenyl, and subsequently to the corresponding 5-ethyl analogs by successive catalytic hydrogenation reactions. The 5-azido substituted analogs can be prepared from the corresponding 5-bromo compounds by reaction with lithium azide in N,N-dimethylformamide. 5-Alkylthio substituted analogs can be prepared from the corresponding 5-bromo compound by reaction with an appropriate alkylmercaptan in the presence of sodium using techniques known to those skilled in the art of organic synthesis.

A number of 5-substituted analogs of the aforementioned compounds can be synthesized from the corresponding 5-amino compounds via the 5-diazonium salt intermediates. Among the other 5-substituted analogs that can be produced from 5-diazonium salt intermediates are: 5-hydroxy analogs, 5-fluoro analogs, 5-chloro analogs, 5-bromo analogs, 5-iodo analogs, 5-cyano analogs, and 5-mercapto analogs. These compounds can be synthesized using the general techniques set forth in C. Zwart et al., supra. For example, 5-hydroxy substituted analogs can be prepared from the reaction of the corresponding 5-diazonium salt intermediates with water. 5-Fluoro substituted analogs can be prepared from the reaction of the 5-diazonium salt intermediates with fluoroboric acid. 5-Chloro substituted analogs can be prepared from the reaction of the 5-amino compounds with sodium nitrite and hydrochloric acid in the presence of copper chloride. 5-Cyano substituted analogs can be prepared from the reaction of the corresponding 5-diazonium salt intermediates with potassium copper cyanide. 5-Amino substituted analogs can also be converted to the corresponding 5-nitro analogs by reaction with fuming sulfuric acid and peroxide, according to the general techniques described in Y. Morisawa, *J. Med. Chem.* 20: 129–133 (1977) for converting an aminopyridine to a nitropyridine. Appropriate 5-diazonium salt intermediates can also be used for the synthesis of mercapto substituted analogs using the general techniques described in J. M. Hoffman et al., *J Med. Chem.* 36: 953–966 (1993). The 5-mercapto substituted analogs can in turn be converted to the 5-alkylthio substituted analogs by reaction with sodium hydride and an appropriate alkyl bromide. 5-Acylamido analogs of the aforementioned compounds can be prepared by reaction of the corresponding 5-amino compounds with an appropriate acid anhydride or acid chloride using techniques known to those skilled in the art of organic synthesis.

5-Hydroxy substituted analogs of the aforementioned compounds can be used to prepare corresponding 5-alkanoyloxy substituted compounds by reaction with the appropriate acid, acidchloride, or acid anhydride. 5-Cyano substituted analogs of the aforementioned compounds can be hydrolyzed to afford the corresponding 5-carboxamido substituted compounds. Further hydrolysis results in formation of the corresponding 5-carboxylic acid substituted analogs. Reduction of the 5-cyano substituted analogs with lithium aluminum hydride yields the corresponding 5-aminomethyl analogs. 5-Acyl substituted analogs can be prepared from corresponding 5-carboxylic acid substituted analogs by reaction with an appropriate alkyl lithium using techniques known to those skilled in the art.

5-Carboxylic acid substituted analogs of the aforementioned compounds can be converted to the corresponding esters by reaction with an appropriate alcohol and acid catalyst. Compounds with an ester group at the 5-pyridyl position can be reduced with sodium borohydride or lithium aluminum hydride to produce the corresponding 5-hydroxyalkyl (e.g., 5-hydroxymethyl) substituted analogs. These analogs in turn can be converted to compounds bearing an ether moiety at the 5-pyridyl position by reaction with sodium hydride and an appropriate alkyl halide, using conventional techniques. Alternatively, the 5-hydroxymethyl substituted analogs can be reacted with tosyl chloride to provide the corresponding 5-tosyloxymethyl analogs. The 5-carboxylic acid substituted analogs can also be converted to the corresponding 5-alkylaminoacyl analogs by reaction with an appropriate alkylamine and thionyl chloride. 5-Acyl substituted analogs of the aforementioned compounds can be prepared from the reaction of the appropriate 5-carboxylic acid substituted compounds with an appropriate alkyl lithium salt, using techniques known to those skilled in the art of organic synthesis.

5-Tosyloxymethyl substituted analogs of the aforementioned compounds can be converted to the corresponding 5-methyl substituted compounds by reduction with lithium aluminum hydride. 5-Tosyloxymethyl substituted analogs of the aforementioned compounds can also be used to produce 5-alkyl substituted compounds via reaction with an alkyl lithium salt. 5-Hydroxy substituted analogs of the aforementioned compounds can be used to prepare 5-N-alkylcarbamoyloxy substituted compounds by reaction with N-alkylisocyanates. 5-Amino substituted analogs of the aforementioned compounds can be used to prepare 5-N-alkoxycarboxamido substituted compounds by reaction with alkyl chloroformate esters, using techniques known to those skilled in the art of organic synthesis. Analogous chemistries to those described hereinbefore, for the preparation of the 5-substituted analogs of the azabicyclo analogs, can be devised for the synthesis of 2-, 4-, and 6-substituted analogs. For example, a number of 2-, 4-, and 6-aminopyridyl azabicyclo compounds can be converted to the corresponding diazonium salt intermediates, which can be transformed to a variety of compounds with substituents at the 2-, 4-, and 6-positions of the pyridine ring as was described for the 5-substituted analogs above.

The present invention relates to nicotinic antagonists. The present invention also relates to methods for providing prevention or treatment of conditions or disorders in a subject susceptible to such a condition or disorder, and for providing treatment to a subject suffering from a condition or disorder. For example, the method comprises administering to a patient an amount of a compound effective for providing some degree of prevention of the progression of a disorder such as a CNS disorder (i.e., provide protective effects), amelioration of the symptoms of the disorder, and/or amelioration of the reoccurrence of the disorder. In particular, the methods of the present invention comprise administering to a patient in need thereof, an amount of a compound selected from the group of compounds of general formulae set forth hereinbefore, which amount is effective to prevent or treat the condition or disorder affecting the patient. The present invention further relates to pharmaceutical compositions incorporating the compounds of general formulae set forth hereinbefore.

The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, salicylate, p-toluenesulfonate, benzoate, benzene sulfonate, and ascorbate; salts with acidic amino acids such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N-dibenzylethylenediamine salt; and salts with basic amino acids such as the lysine salt and arginine salts. The salts may in some cases be hydrates or ethanol solvates.

The compounds of the present invention are beneficial in therapeutic applications requiring a selective inhibition at certain nicotinic receptor subtypes; that is, the compounds are antagonists at certain nicotinic receptor subtypes. The pharmaceutical compositions of the present invention are useful for the prevention and treatment of a wide variety of conditions or disorders. The compounds of the present invention are useful for treating certain CNS conditions and disorders; such as in providing neuroprotection, in treating patients susceptible to convulsions, in treating depression, in treating autism, in treating Tourette's syndrome, in treating certain neuroendocrine disorders, and in the management of stroke. The compounds of the present invention also are useful in treating hypertension, for effecting weight loss, in treating type II diabetes and neoplasia, or as anti-bacterial or antiviral agents. The compounds of the present invention also are useful, when appropriately radio-labeled, as probes in life science applications (e.g., as selective probes in neuroimaging applications). For example, compounds of the present invention can be used to inhibit interaction of viral proteins with nicotinic receptors. See, Bracci et al., *FEBS Letters*. 311(2): 115–118 (1992). See also, for example, the types of conditions and disorders that are treated using nicotinic compounds, as set forth in PCT WO 94/08992 and PCT WO 96/31475, U.S. Pat. Nos. 5,583,140 to Bencherif et al., 5,597,919 to Dull et al. and 5,604,231 to Smith et al., and U.S. patent application Ser. No. 09/054,175, filed Apr. 2, 1998.

The pharmaceutical compositions of the present invention can also include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein by reference in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; opthamalically, intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can-be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes (e.g., those which have an effect upon the functioning of the CNS), while minimizing the effects upon receptor subtypes in muscle and ganglia. Other suitable methods for administering the compounds of the present invention are described in U.S. Pat. No. 5,604,231 to Smith et al., the disclosure of which is incorporated herein by reference in its entirety.

Compounds of the present invention bind to relevant receptors and, are antagonists (i.e., inhibit the function of relevant receptor subtypes). Concentrations, determined as the amount of compound per volume of receptor-containing tissue, typically provide a measure of the degree to which that compound binds to and affects relevant receptor subtypes. The compounds of the present invention are selective in that at relevant concentrations (i.e., low concentrations) those compounds bind to, and have inhibitory effects upon, receptors associated with the modulation of neurotransmitters.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1.5. The log P values of such typical compounds generally are less than about 4, often are less than about 3.5, and frequently are less than about 3.0. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause inhibition of, nicotinic receptors of the brain of the patient. As such, these compounds have the ability to express nicotinic pharmacology, and in particular, to act as nicotinic antagonists. The receptor binding constants of typical compounds useful in carrying out the present invention generally exceed about 500 nM, often exceed about 100 nM, and frequently exceed about 50 nM. The receptor binding constants of such typical compounds generally are less than about 1 uM, often are less than about 100 nM, and frequently are less than about 20 nM. Receptor binding constants provide a measure of the ability of the compound to bind to half of the relevant receptor sites of certain brain cells of the patient. See, Cheng, et al., *Biochem. Pharmacol.* 22:3099 (1973).

The appropriate dose of the compound is that amount effective to prevent occurrence of the symptoms of the condition or disorder, or to treat some symptoms of the condition or disorder from which the patient suffers. By "effective amount", "therapeutic amount" or "effective dose" is meant that amount sufficient to elicit the desired pharmacological or therapeutic effects, thus resulting in effective prevention or treatment of the condition or disorder. Thus, when treating a CNS disorder, an effective amount of compound is an amount sufficient to pass across the blood-brain barrier of the subject, to bind to relevant receptor sites in the brain of the subject, and to inhibit relevant nicotinic receptor subtypes (e.g., inhibits neurotransmitter secretion, thus resulting in effective prevention or treatment of the disorder). Prevention of the condition or disorder is manifested by delaying the onset of the symptoms of the condition or disorder Treatment of the condition or disorder is manifested by a decrease in the symptoms associated with the condition or disorder, or an amelioration of the reoccurrence of the symptoms of the condition or disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to inhibit relevant receptors to effect neurotransmitter release but the amount should be insufficient to induce effects on skeletal muscles and ganglia to any significant degree. The effective dose of compounds will of course differ from patient to patient but in general includes amounts starting where desired therapeutic effects are observed but below the amounts where muscular effects are observed.

Typically, the effective dose of compounds generally requires administering the compound in an amount of less than 1 ug/kg of patient weight. Often, the compounds of the present invention are administered in an amount from 10 ng to less than 1 ug/kg of patient weight, frequently between about 0.1 ug to less than 1 ug/kg of patient weight, and preferably between about 0.1 ug to about 0.5 ug/kg of patient weight. Compounds of the present invention can be administered in an amount of 0.3 to 0.5 ug/kg of patient weight. For compounds of the present invention that do not induce effects on muscle or ganglion-type nicotinic receptors at low concentrations, the effective dose is less than 50 ug/kg of patient weight; and often such compounds are administered in an amount from 0.5 ug to less than 50 ug/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./ patient. For human patients, the effective dose of typical compounds requires administering the compound which generally does not exceed about 500, often does not exceed about 400, and frequently does not exceed about 300 ug/24 hr./ patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to demonstrate a nicotinic function by effectively inhibiting neurotransmitter secretion from nerve ending preparations (i.e., synaptosomes). As such, such compounds have the ability to inhibit relevant neurons to release or secrete acetylcholine, dopamine, and other neurotransmitters. Generally, typical compounds useful in carrying out the present invention provide for the inhibition of dopamine secretion in amounts of at least one third, typically at least about 10 times less, frequently at least about 100 times less, and sometimes at least about 1,000 times less, than those required for activation of muscle or ganglion-type nicotinic receptors.

The compounds of the present invention, when employed in effective amounts in accordance with the method of the present invention, are selective to certain relevant nicotinic receptors, but do not cause significant activation of receptors associated with undesirable side effects at concentrations at least 10 times higher than those required for inhibition of dopamine release. By this is meant that a particular dose of compound resulting in prevention and/or treatment of a CNS disorder, is essentially ineffective in eliciting activation of certain ganglionic-type nicotinic receptors at concentration higher than 5 times, preferably higher than 100 times, and more preferably higher than 1,000 times, than those required for inhibition of dopamine release. This selectivity of certain compounds of the present invention against those receptors responsible for cardiovascular side effects is demonstrated by a lack of the ability of those compounds to activate nicotinic function of adrenal chromaffin tissue at concentrations at least 10 times greater than those required for inhibition of dopamine release.

Compounds of the present invention, when employed in effective amounts in accordance with the method of the present invention, are effective towards providing some degree of prevention of the progression of certain conditions and disorders, amelioration of the symptoms of those conditions and disorders, an amelioration to some degree of the reoccurrence of those conditions and disorders. However, such effective amounts of those compounds are not sufficient to elicit any appreciable side effects, as demonstrated by increased effects relating to the cardiovascular system, and effects to skeletal muscle. As such, administration of certain compounds of the present invention provides a therapeutic window in which treatment of certain conditions and disorders is provided, and side effects are avoided. That is, an effective dose of a compound of the present invention is sufficient to provide the desired effects upon relevant nicotinic receptor subtypes, but is insufficient (i.e., is not at a high enough level) to provide undesirable side effects. Preferably, effective administration of a compound of the present invention resulting in treatment of a wide variety of conditions and disorders occurs upon administration of less than 1/5, and often less than 1/10 that amount sufficient to cause any side effects to a significant degree.

The following examples are provided to further illustrate the present invention, and should not be construed as limiting thereof.

EXAMPLE 1

Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., *Biochem, Pharmacol.* 22:3099 (1973).

EXAMPLE 2
Determination of Binding to Alpha 7 type Receptor Sites

Sprague-Dawley rats were purchased from The Harlan Co. (Indiana, U.S.A.) and maintained on a 12 hour light/dark cycle with water and standard Purina Rat Chow ad libitum. Rats were sacrificed using $CO_2$ anesthesia followed by decapitation and hippocampi were isolated and processed according to previously described protocols (Bencherif et al., 1996). Cells were harvested in cold Tris buffer (5 mM, pH 7.4), and homogenized with a Polytron (Brinkmann Instruments, NY; settings at full power for 10 seconds). The homogenate was centrifuged at 40,000×g for 10 minutes, the supernatant was discarded, and the pellet was reconstituted in PBS (pH 7.4). Standard procedures for ligand binding studies were followed and sample aliquots were reserved for determination of protein concentration with bovine serum albumin as the standard. Equilibrium binding assays were conducted at room temperature by incubating membrane aliquots suspended in 300 ul assay buffer with 10 nM $^{125}$I-labeled monoiodinated α-bungarotoxin (I-Bgt) (Dupont, NEN). Non-specific binding was determined in samples supplemented with 10 uM nicotine or 1 mM carbachol. Incubation was terminated by rapid filtration on a multimanifold tissue harvester (Brandel) using G/C filters presoaked in 0.33% polyethyleneimine. Samples were processed for specific radioligand binding assays using $^{125}$I-labelled monoiodinated α-bungarotoxin (I-Bgt) obtained from New England Nuclear (NEN). Reagents were purchased from Sigma Chemical Co. and were of the highest available grade. Radiolabelled ligands were purchased from New England Nuclear (NEN).

EXAMPLE 3
Determination of Receptor Activation/Inhibition and Dopamine Release Dopamine release was measured using the techniques described in U.S. Pat. No. 5,597,919 to Dull et al. Release is expressed as a percentage of release obtained with a concentration of (S)-(−)-nicotine resulting in maximal effects. Reported $EC_{50}$ values are expressed in nM, and $E_{max}$ values represent the amount released relative to (S)-(−)-nicotine or tetramethylammonium ion (TMA), on a percentage basis.

Isotopic rubidium release was measured using the techniques described in Bencherif et al., *JPET*, 279: 1413–1421 (1996). Reported $EC_{50}$ values are expressed in nM, and $E_{max}$ values represent the amount of rubidium ion released relative to 300 uM tetramethylammonium ion, on a percentage basis.

Reported $IC_{50}$ values are expressed in nM and represent the concentration resulting in 50% inhibition of agonist induced receptor activation. $E_{max}$ values represent the amount released relative to (S)-(−)-nicotine on a percentage basis.

EXAMPLE 4
Determination of Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported $EC_{50}$ values are expressed in nM, and $E_{max}$ values represent the amount released relative to (S)-(−)-nicotine on a percentage basis.

EXAMPLE 5
Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

EXAMPLE 6
Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ a values represent the amount released relative to (S)-(−)-nicotine on a percentage basis.

EXAMPLE 7
Determination of Log P Value

Log P values, which have been used to assess the relative abilities of compounds to pass across the blood-brain barrier (Hansch, et al., *J. Med. Chem. ii:*1 (1968)), were calculated using the Cerius$^2$ software package Version 3.5 by Molecular Simulations, Inc.

EXAMPLE 8

Sample No. 1 is 2-((3-pyridyl)methyl)-1-azabicyclo [2.2.2]octane, which was prepared in accordance with the following techniques:

Quinuclidin-3-one hydrochloride (4.6 g, 28.3 mmol) and powdered anhydrous potassium hydroxide (2.1 g, 37.2 mmol) were dissolved in methanol (25 ml) and stirred for 15 mins. Pyridine-3-carboxaldehyde (3.2 g, 29.5 mmol) was then added in one portion and the mixture was stirred for an additional 20 hrs. The reaction mixture was then diluted with 40 m water and cooled to 0° C. yielding 2-((3-pyridyl) methylene)-1-azabicyclo[2.2.2]octan-3-one as a yellow precipitate, which was collected, washed with distilled water and dried under vacuum (5.16 g, 81.4%). 2-((3-Pyridyl) methylene)-1-azabicyclo[2.2.2]octan-3-one (3 g, 14.0 mmol) was dissolved in 200 ml methanol and sodium borohydride (3 g, 79.6 mmol) was added in portions (exothermic reaction) with vigorous stirring. After 1 hr of continued stirring, acetone (100 ml) was slowly added to neutralize the remaining borohydride reagent. The mixture was evaporated to dryness and the resulting residue suspended in water (200 ml) and extracted three times with 200 ml portions of chloroform. The chloroform phases were combined, dried over $MgSO_4$, and rotary evaporated to give a clear oil; crystallization of the free base gave a quantitative yield of 2-((3-pyridyl)methylene)-1-azabicyclo[2.2.2]octan-3-ol as a white precipitate. 2-((3-pyridyl)methylene)-1-azabicyclo[2.2.2]octan-3-ol (1 g, 4.7 mmol) was combined with neat thionyl chloride (20 ml, 26.9 mmol) under a nitrogen atmosphere at 0° C., the reaction was than brought to room temperature and stirred for one additional hour. Rotary evaporation at 60° C. produced a viscous oil which, when suspended in ether, afforded 3-chloro-2-((3-Pyridyl) methylene)-1-azabicyclo[2.2.2]octane dihydrochloride as a hygroscopic precipitate (0.98 g, 91%). This chloroquinuclidine (0.3 g, 15 mmol) was dissolved in ethanol (50 ml) and wet Rainey nickel (0.5 g) was carefully added under nitrogen. The suspension was hydrogenated at 50 psig in a Parr hydrogenation apparatus for 6 hrs followed by filtration through a pad of Celite filter aid and additional washing of the pad with methanol. Rotary evaporation of the pooled solvents gave 2-((3-pyridyl)methylene)-1-azabicyclo[2.2.2]

octane as a clear oil that solidified upon cooling (0.2 g, 70%). This material (120 mg) was dissolved in 50 ml methanol followed by the careful addition of 0.1 g 10% palladium on charcoal. The suspension was hydrogenated at 50 psig in a Parr hydrogenation apparatus for 28 hrs followed by filtration through a pad of Celite filter aid and additional washing of the pad with methanol. Evaporation of the solvents afforded a white residue which was crystallized from ethanol-ether to give the desired material, 2-((3-pyridyl)methyl)-1-azabicyclo[2.2.2]octane, as a white solid (99 mg, 81%).

Sample No. 1 exhibits a log P of 1.99, and such a favorable log P value indicates that the compound has the capability of passing the blood-brain barrier. The compound exhibits a Ki of 37 nM at $\alpha4\beta2$ receptor subtypes and a Ki of 50 uM at $\alpha7$ receptor subtypes, indicating selectivity to each of those receptor subtypes. The binding constant indicates that the compound exhibits high affinity binding to certain relevant CNS nicotinic receptors.

Sample No. 1 exhibits an $E_{max}$ value of 0% (at 100 uM) for dopamine release. Sample No. 1 exhibits an $E_{max}$ value of 20% (at 100 uM) at muscle-type receptors, indicating that the compound minimally induces activation of muscle-type receptors. The sample exhibits an $E_{max}$ value of 78% (at 100 uM) at ganglionic-type receptors.

EXAMPLE 9

Sample No. 2 is 2-((3-pyridyl)methyl)-1-azabicyclo[2.2.2]octan-3-one, which was prepared in accordance with the following techniques:

Quinuclidin-3-one hydrochloride (4.6 g, 28.3 mmol) and powdered anhydrous potassium hydroxide (2.1 g, 37.2 mmol) were dissolved in methanol (25 ml) and stirred for 15 mins. Pyridine-3-carboxaldehyde (3.2 g, 29.5 mmol) was then added in one portion and the mixture was stirred for an additional 20 hrs. The reaction mixture was then diluted with 40 ml water and cooled to 0° C. yielding 2-((3-pyridyl)methylene)-1-azabicyclo[2.2.2]octan-3-one as a yellow precipitate, which was collected, washed with distilled water and dried under vacuum (5.16 g, 81.4%). 2-((3-Pyridyl)methylene)-1-azabicyclo[2.2.2]octan-3-one (1.0 g, 4.7 mmol) was combined with 50 ml methanol and 0.2 g palladium on charcoal (5% w/w) in a hydrogenation vessel. Hydrogenation (50 psig) was carried out for 4 hrs., after which time the slurry was carefully filtered through a pad of Celite filter aid. Evaporation of solvent gave 2-((3-pyridyl)methyl)-1-azabicyclo[2.2.2]octan-3-one as white semisolid, which dissolved in ethanol give a white crystalline solid upon cooling (0.82 g 88%).

Sample No. 2 exhibits a log P of 0.882, and such a favorable log P value indicates that the compound has the capability of passing the blood-brain barrier. The compound exhibits a Ki of 473 nM at $\alpha4\beta2$ receptor subtypes, indicating selectivity for that receptor subtype. The binding constant indicates that the compound exhibits high affinity binding to certain CNS nicotinic receptors.

Sample No. 2 exhibits an $E_{max}$ value of 0% (at 100 uM) for dopamine release. Sample No. 2 exhibits $E_{max}$ value of 0% (at 100 uM) at muscle-type receptors, indicating that the compound does not induce activation of muscle-type receptors to any significant degree. Sample No. 2 exhibits an $E_{max}$ value of 0% (at 100 uM) ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglion effects to any significant degree.

EXAMPLE 10

Sample No. 3 is 2-((3-pyridyl)methyl)-1-azabicyclo[2.2.2]oct-2-ene which was prepared in accordance with the following techniques:

Quinuclidin-3-one hydrochloride (4.6 g, 28.3 mmol) and powdered anhydrous potassium hydroxide (2.1 g, 37.2 mmol) were dissolved in methanol (25 ml) and stirred for 15 mins. Pyridine-3-carboxaldehyde (3.2 g, 29.5 mmol) was then added in one portion and the mixture was stirred for an additional 20 hrs. The reaction mixture was then diluted with 40 ml water and cooled to 0° C. yielding 2-((3-pyridyl)methylene)-1-azabicyclo[2.2.2]octan-3-one as a yellow precipitate, which was collected, washed with distilled water and dried under vacuum (5.16 g, 81.4%). 2-((3-Pyridyl)methylene)-1-azabicyclo[2.2.2]octan-3-one (3 g, 140 mmol) was dissolved in 200 ml methanol and sodium borohydride (3 g, 79.6 mmol) was added in portions (exothermic reaction) with vigorous stirring. After 1 hr of continued stirring, acetone (100 ml) was slowly added to neutralize the remaining borohydride reagent. The mixture was evaporated to dryness and the resulting residue suspended in water (200 ml) and extracted three times with 200 ml portions of chloroform. The chloroform phases were combined, dried over $MgSO_4$, and rotary evaporated to give a clear oil; crystallization of the free base gave a quantitative yield of 2-((3-pyridyl)methylene)-1-azabicyclo[2.2.2]octan-3-ol as a white precipitate. 2-((3-Pyridyl)methylene)-1-azabicyclo[2.2.2]octan-3-ol (1 g, 4.7 mmol) was combined with neat thionyl chloride (20 ml, 26.9 mmol) stirred under a nitrogen atmosphere at 0° C., the reaction was than brought to room temperature and stirred for one additional hour. Rotary evaporation at 60° C. produced a viscous oil which when suspended in ether afforded 3-chloro-2-((3-pyridyl)methylene)-1-azabicyclo[2.2.2]octane dihydrochloride as a hygroscopic precipitate (0.98 g, 91%). The chloroquinuclidine (0.3 g, 1.3 mmol) was combined with 50 ml ethanol in a hydrogenation vessel, then wet Raney nickel (2.5 grams) was added in one portion. Hydrogenation (50 psig) was carried out for 6 hrs., after which time the slurry was carefully filtered through a pad of Celite filter aid. Evaporation of solvent gave the desired 2-((3-pyridyl)methylene)-1-azabicyclo[2.2.2]octane dihydrochloride as a white reside which easily recrystallized from ethanol-ether to give a white crystalline solid (0.21 g 70%).

Sample No. 3 exhibits a log P of 0.79, and such a favorable log P value indicates that the compound has the capability of passing the blood-brain barrier. The compound exhibits a Ki of 73 nM at $\alpha4\beta2$ receptor subtypes and a Ki of 35 nM at $\alpha7$ receptor subtypes. The low binding constant indicates that the compound exhibits good high affinity binding to certain relevant CNS nicotinic receptors.

Sample No. 3 exhibits an $E_{max}$ value of 0% (at 100 uM) for dopamine release. Sample No. 3 exhibits $EC_{50}$ of 2uM and an $E_{max}$ value of 100% at muscle-type receptors, indicating that the compound does not induce activation of muscle-type receptors to any significant degree. Sample No. 3 exhibits an $EC_{50}$ of 2 uM and an $E_{max}$ value of 115% at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglion effects to any significant degree.

EXAMPLE 11

Sample No. 4 is 2-((3-pyridyl)methyl)-1-azabicyclo [2.2.2]octan-3-ol, which was prepared in accordance with the following techniques:

Quinuclidin-3-one hydrochloride (4.6 g, 28.3 mmol) and powdered anhydrous potassium hydroxide (2.1 g, 37.2 mmol) were dissolved in methanol (25 ml) and stirred for 15 mins. Pyridine-3-carboxaldehyde (3.2 g, 29.5 mmol) was then added in one portion and the mixture was stirred for an additional 20 hrs. The reaction mixture was then diluted with 40 ml water and cooled to 0° C. yielding 2-((3-pyridyl) methylene)-1-azabicyclo[2.2.2]octan-3-one as a yellow precipitate, which was collected, washed with distilled water and dried under vacuum (5.16 g, 81.4%). 2-((3-Pyridyl) methylene)-1-azabicyclo[2.2.2]octan-3-one (1.0 g, 4.7 mmol) was combined with 50 ml methanol in a hydrogenation vessel, then wet Raney nickel (5 grams) was added in one portion. Hydrogenation (50 psig) was carried out for 12 hrs., after which time the slurry was carefully filtered through a pad of Celite filter aid. Evaporation of solvent gave 2-((3-pyridyl)methyl)-1-azabicyclo[2.2.2]octan-3-ol as a light yellow oil, which dissolved in ethanol/HCl give a white crystalline solid upon cooling (0.78 g 77%).

Sample No. 4 exhibits a log P of 1.21, and such a favorable log P value indicates that the compound has the capability of passing the blood-brain barrier. The compound exhibits a Ki of 1.2 uM at α4β2 receptor subtypes. The binding constant indicates that the compound exhibits high affinity binding to certain CNS nicotinic receptors.

Sample No. 4 exhibits an $E_{max}$ value of 0% (at 100 uM) for dopamine release. Sample No. 4 exhibits $E_{max}$ value of 0% (at 100 uM) at muscle-type receptors, indicating that the compound does not induce activation of muscle-type receptors to any significant degree. Sample No. 4 exhibits an $E_{max}$ value of 29% (at 100 uM) ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglion effects to any significant degree.

EXAMPLE 12

Sample No. 5 is 2-((3-oxolanyl)methyl)-1-azabicyclo [2.2.2]octan-3-one, which was prepared in accordance with the following techniques:

Quinuclidin-3-one hydrochloride (4.6 g, 28.3 mmol) and powdered anhydrous potassium hydroxide (2.1 g, 37.2 mmol) were dissolved in methanol (25 ml) and stirred for 15 mins. Furan-3-carboxaldehyde (2.83 g, 29.5 mmol) was then added in one portion and the mixture was stirred for an additional 20 hrs. The reaction mixture was then diluted with 40 ml water and cooled to 0° C. yielding 2-((3-furyl) methylene)-1-azabicyclo[2.2.2]octan-3-one as a yellow precipitate, which was collected, washed with distilled water and dried under vacuum (5.16 g, 81.4%). 2-((3-Furyl) methylene)-1-azabicyclo[2.2.2]octan-3-one (2.1 g, 100 mmol) was dissolved in methanol (100 ml) and 10% palladium on charcoal (0.2 g) was carefully added under nitrogen. The suspension was hydrogenated at 50 psig in a Parr hydrogenation apparatus for 8 hrs followed by quenching of the catalyst with a small amount of chloroform. The entire slurry was filtered through a pad of Celite filter aid followed by additional washing of the pad with methanol. Rotary evaporation of the pooled solvents gave the desired product, 2-((3-oxolanyl)methyl)-1-azabicyclo[2.2.2]octan-3-one, as a clear oil that solidified upon cooling (2.05 g, 96.7%).

Sample No. 5 exhibits a log P of 1.05, and such a favorable log P value indicates that the compound has the capability of passing the blood-brain barrier. The compound exhibits a Ki of 5.5 uM at α4β2 receptor subtypes. The binding constant indicates that the compound exhibits high affinity binding to certain CNS nicotinic receptors.

That which is claimed is:

1. A compound having a structure of formula:

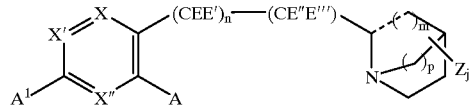

where the dashed line in the structure indicates that the bond can be a C—C or C=C bond; X is carbon; X' and X" are selected from the group consisting of carbon and nitrogen, wherein when X' is nitrogen, X" is carbon, and when X" is nitrogen, X' is carbon; X, and X' and X" when these are carbon, are bonded to a species hereinafter defined as A"; A and A' are individually substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", CF$_3$, OH, CN, NO$_2$, C$_2$R', SH, SR', N$_3$, SO$_2$ R', OR', (CR'R")$_q$OR', O—(CR'R")$_q$ C$_2$R', SR', C(=O)NR'R", NR'C(=O)R", C(=O)R', (CR'R")$_q$C$_2$R', C(=O)OR', OC(=O)R', OC(=O)NR'R" and NR'C(=O)OR" where q is an integer from 1 to 6 and R' and R" are individually hydrogen, alkyl or an aromatic group-containing species; A" is selected from the group consisting of H, NR'R", OR' and NO$_2$ wherein R' and R" are selected from the group consisting of hydrogen, alkyl, cycloalkyl, a non-aromatic heterocyclic ring and an aromatic group-containing species; n is an integer from 0 to 3; m is 0, 1 or 2; p is 1 or 2; E, E', E" and E''' individually represent hydrogen, alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; either E and E' or E" and E''' and their associated carbon atom can combine to form a ring structure; either E and E" or E' and E''' and their associated carbon atoms can combine to form a ring structure; j is an integer from 0 to 3; and Z represents a non-hydrogen substituent selected from the group consisting of alkyl, substituted alkyl, acyl, hydroxy, alkoxy, alkoxycarbonyl, aryloxycarbonyl, and oxygen.

2. The compound of claim 1 wherein A" is selected from the group consisting of NH$_2$, NHCH$_3$ or N(CH$_3$)$_2$.

3. The compound of claim 1 wherein the dashed line is a C=C bond.

4. The compound of claim 1 wherein Z is hydroxy or oxygen.

5. The compound of claim 1, wherein the compound is 2-((3-pyridyl)methyl)-1- azabicyclo[2.2.2]octan-3-one.

6. The compound of claim 1, wherein the compound is 2-((3-pyridyl)methyl)-1- azabicyclo[2.2.2]octan-3-ol.

7. The compound of claim 1, wherein the compound is 2-((3-pyridyl)methyl)-1- azabicyclo[2.2.2]octane.

8. A pharmaceutical composition incorporating a nicotinic antagonist, said composition comprising an amount of a compound of the formula:

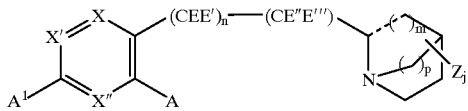

in association with a pharmaceutically acceptable carrier, wherein said amount is effective to interact with relevant nicotinic receptor sites of a patient where the dashed line in the structure indicates that the bond can be a C—C or C=C bond; X is carbon; X' and X" are selected from the group consisting of carbon and nitrogen, wherein when X' is nitrogen, X" is carbon, and when X" is nitrogen, X' is carbon; X, and X' and X" when these are carbon, are bonded to a species hereinafter defined as A"; A and A' are individually substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", CF$_3$, OH, CN, NO$_2$, C$_2$R', SH, SR', N$_3$, SO$_2$R', OR', (CR'R")$_q$OR', O—(CR'R")$_q$C$_2$R', C(=O)NR'R", NR'C(=O)R", C(=O)R', (CR'")$_q$C$_2$R', C(=O)OR', OC(=O)R', OC(=O)NR'R" and NR'C(=O)OR" where q is an integer from 1 to 6 and R' and R" are individually hydrogen, alkyl or an aromatic group-containing species; A" is selected from the group consisting of H, NR'R", OR' and NO$_2$ wherein R' and R" are selected from the group consisting of hydrogen, alkyl, cycloalkyl, a non-aromatic heterocyclic ring and an aromatic group-containing species; n is an integer from 0 to 3; m is 0, 1 or 2; p is 1 or 2; E, E', E" and E'" individually represent hydrogen, alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; either E and E' or E" and E'" and their associated carbon atom can combine to form a ring structure; either E and E" or E' and E'" and their associated carbon atoms can combine to form a ring structure; j is an integer from 0 to 3; and Z represents a non-hydrogen substituent selected from the group consisting of alkyl, substituted alkyl, acyl, hydroxy, alkoxy, alkoxycarbonyl, aryloxycarbonyl, and oxygen.

9. The pharmaceutical composition of claim 8 wherein A" is selected from the group consisting of NH$_2$, NHCH$_3$ or N(CH$_3$)$_2$.

10. The pharmaceutical composition of claim 8 wherein the dashed line is a C=C bond.

11. The pharmaceutical composition of claim 8 wherein Z is hydroxy or oxygen.

12. The pharmaceutical composition of claim 8, wherein the compound is 2-((3- pyridyl)methyl)-1-azabicyclo[2.2.2]octan-3-one.

13. The pharmaceutical composition of claim 8, wherein the compound is 2-((3- pyridyl)methyl)-1-azabicyclo[2.2.2]octan-3-ol.

14. The pharmaceutical composition of claim 8, wherein the compound is 2-((3- pyridyl)methyl)-1-azabicyclo[2.2.2]octane.

15. A method of treating depression comprising administering to a subject in need of such treatment an effective amount of a compound of the formula:

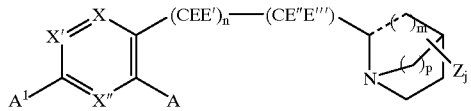

where the dashed line in the structure indicates that the bond can be a C—C or C=C bond; X is carbon; X' and X" are selected from the group consisting of carbon and nitrogen, wherein when X' is nitrogen, X" is carbon, and when X" is nitrogen, X' is carbon; X, and X' and X" when these are carbon, are bonded to a species hereinafter defined as A"; A and A' are individually substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", CF$_3$, OH, CN, NO$_2$, C$_2$R', SH, SR', N$_3$, SO$_2$R', OR', (CR'R")$_q$OR', O—(CR'R")$_q$C$_2$R', C(=O)NR'R", NR'C(=O)R", C(=O)R', (CR'R")$_q$C$_2$R', C(=O)OR', OC(=O)R', OC(=O)NR'R" and NR'C(=O)OR" where q is an integer from 1 to 6 and R' and R" are individually hydrogen, alkyl or an aromatic group-containing species; A" is selected from the group consisting of H, NR'R" OR' and NO$_2$ wherein R' and R" are selected from the group consisting of hydrogen, alkyl, cycloalkyl, a non-aromatic heterocyclic ring and an aromatic group-containing species; n is an integer from 0 to 3; m is 0, 1 or 2; p is 1 or 2; E, E', E" and E'" individually represent hydrogen, alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; either E and E' or E" and E'" and their associated carbon atom can combine to form a ring structure; either E and E" or E' and E'" and their associated carbon atoms can combine to form a ring structure; j is an integer from 0 to 3; and Z represents a non-hydrogen substituent selected from the group consisting of alkyl, substituted alkyl, acyl, hydroxy, alkoxy, alkoxycarbonyl, aryloxycarbonyl, and oxygen.

16. The method of claim 15 wherein A" is selected from the group consisting of NH$_2$, NHCH$_3$ or N(CH$_3$)$_2$.

17. The method of claim 15 whereby the dashed line is a C=C bond.

18. The method of claim 15 wherein Z is hydroxy or oxygen.

19. The method of claim 15, wherein the compound is 2-((3-pyridyl)methyl)-1- azabicyclo[2.2.2]octan-3-one.

20. The method of claim 15, wherein the compound is 2-((3-pyridyl)methyl)-1- azabicyclo[2.2.2]octan-3-ol.

21. The method of claim 15, wherein the compound is 2-((3-pyridyl)methyl)-1- azabicyclo[2.2.2]octane.

22. A compound having a structure of the formula:

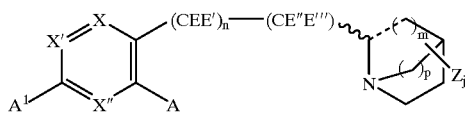

where the wavy line in the structure indicates a C—C bond; the dashed line in the structure indicates that the bond can be a C—C or C=C bond; X is carbon; X' and X" are selected from the group consisting of carbon and nitrogen, wherein when X' is nitrogen, X" is carbon, and when X" is nitrogen, X' is carbon; X, and X' and X" when these are carbon, are bonded to a species hereinafter defined as A"; A and A' are individually substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I NR'R", CF$_3$, OH, CN, NO$_2$, C$_2$R', SH, SR', N$_3$, SO$_2$R', OR', (CR'R")$_q$OR', O—(CR'R")$_q$C$_2$R', C(=O)NR'R", NR'C(=O)R", C(=O)R', (CR'R")$_q$C$_2$R', C(=O)OR', OC(=O)R', OC(=O)NR'R" and NR'C(=O)OR" where q is an integer from 1 to 6 and R' and R" are individually hydrogen, alkyl or an aromatic group containing species; A" is selected from the group consisting of H, NR'R", OR' and NO$_2$ wherein R' and R" are selected from the group consisting of hydrogen, alkyl, cycloalkyl, a non-aromatic heterocyclic ring and an aromatic group-containing species; n is an integer from 0 to 3; m is 0, 1 or 2; p is 1 or 2; E, E', E" and E''' individually represent hydrogen, alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; either E and E" or E' and E''' and their associated carbon atom can combine to form a ring structure; either E and E" or E' and E''' and their associated carbon atoms can combine to form a ring structure; j is 1; and Z is hydroxy or oxygen.

23. The compound of claim 22, wherein A" is selected from the group consisting of NH$_2$, NHCH$_3$ or N(CH$_3$)$_2$.

24. The compound of claim 22, wherein the dashed line is a C=C bond.

25. A pharmaceutical composition incorporating a nicotinic antagonist, said composition comprising an amount of a compound of the formula:

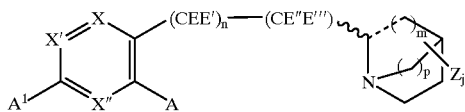

in association with a pharmaceutically acceptable carrier, wherein said amount is effective to interact with relevant nicotinic receptor sites of a patient where the wavy line in the structure indicates a C—C bond; the dashed line in the structure indicates that the bond can be a C—C or C=C bond; X is carbon; X' and X" are selected from the group consisting of carbon and nitrogen, wherein when X' is nitrogen, X" is carbon, and when X" is nitrogen, X' is carbon; X, and X' and X" when these are carbon, are bonded to a species hereinafter defined as A"; A and A' are individually substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", CF$_3$, OH, CN, NO$_2$, C$_2$R', SH, SR', N$_3$, SO$_2$ R', OR', (CR'R")$_q$OR', O—(CR'R")$_q$C$_2$R', C(=O)NR'R", NR'C(=O)R", C(=O)R', (CR'R")$_q$C$_2$R', C(=O)OR', OC(=O)R', OC(=O)NR'R" and NR'C(=O)OR" where q is an integer from 1 to 6 and R' and R" are individually hydrogen, alkyl or an aromatic group containing species; A" is selected from the group consisting of H, NR'R", OR' and NO$_2$ wherein R' and R" are selected from the group consisting of hydrogen, alkyl, cycloalkyl, a non-aromatic heterocyclic ring and an aromatic group-containing species; n is an integer from 0 to 3; m is 0, 1 or 2; p is 1 or 2; E, E', E" and E''' individually represent hydrogen, alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; either E and E' or E" and E''' and their associated carbon atom can combine to form a ring structure; either E and E" or E' and E''' and their associated carbon atoms can combine to form a ring structure; j is 1; and Z is hydroxy or oxygen.

26. The pharmaceutical composition of claim 25, wherein A" is selected from the group consisting of NH$_2$, NHCH$_3$ or N(CH$_3$)$_2$.

27. The pharmaceutical composition of claim 25, wherein the dashed line is a C=C bond.

28. A method of treating depression comprising administering to a subject in need of such treatment an effective amount of a compound of the formula:

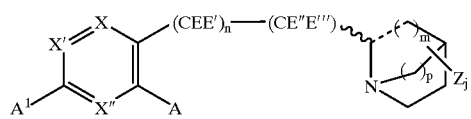

where the wavy line in the structure indicates a C—C bond; the dashed line in the structure indicates that the bond can be a C—C or C=C bond; X is carbon; X' and X" are selected from the group consisting of carbon and nitrogen, wherein when X' is nitrogen, X" is carbon, and when X" is nitrogen, X' is carbon; X, and X' and X" when these are carbon, are bonded to a species hereinafter defined as A"; A and A' are individually substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", CF$_3$, OH, CN, NO$_2$, C$_2$R', SH, SR', N$_3$, SO$_2$R', OR', (CR'R")$_q$OR', O—(CR'R")$_q$C$_2$R', C(=O)NR'R", NR'C(=O)R", C(=O)R', (CR'R")$_q$C$_2$R', C(=O)OR', OC(=O)R', OC(=O)NR'R" and NR'C(=O)OR" where q is an integer from 1 to 6 and R' and R" are individually hydrogen, alkyl or an aromatic group containing species; A" is selected from the group consisting of H, NR'R", OR' and NO$_2$ wherein R' and R" are selected from the group consisting of hydrogen, alkyl, cycloalkyl, a non-aromatic heterocyclic ring and an aromatic group-containing species; n is an integer from 0 to 3; m is 0, 1 or 2; p is 1 or 2; E, E', E" and E''' individually represent hydrogen, alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; either E and E' or E" and E''' and their associated carbon atom can combine to form a ring structure; either E and E" or E' and E''' and their associated carbon atoms can combine to form a ring structure; j is 1; and Z is hydroxy or oxygen.

29. The method of claim 28, wherein A" is selected from the group consisting of NH$_2$, NHCH$_3$ or N(CH$_3$)$_2$.

30. The method of claim 28, wherein the dashed line is a C=C bond.

* * * * *